United States Patent
Muniz-Medina et al.

(10) Patent No.: US 9,427,279 B2
(45) Date of Patent: Aug. 30, 2016

(54) SURGICAL TOOL ARRANGEMENT HAVING A HANDPIECE USABLE WITH MULTIPLE SURGICAL TOOLS

(75) Inventors: Pedro Javier Muniz-Medina, Caguas, PR (US); Michael G. Hilldoerfer, Sunnyvale, CA (US); Sean M. Darby, San Jose, CA (US); Reid S. Cover, Mountain View, CA (US); Wenjie Deng, San Jose, CA (US)

(73) Assignee: STRYKER CORPORATION, Kalamazoo, MI (US)

( * ) Notice: Subject to any disclaimer, the term of this patent is extended or adjusted under 35 U.S.C. 154(b) by 1350 days.

(21) Appl. No.: 13/138,194

(22) PCT Filed: Jan. 25, 2010

(86) PCT No.: PCT/US2010/000202
§ 371 (c)(1),
(2), (4) Date: Jul. 18, 2011

(87) PCT Pub. No.: WO2010/098809
PCT Pub. Date: Sep. 2, 2010

(65) Prior Publication Data
US 2011/0301578 A1    Dec. 8, 2011

(51) Int. Cl.
*A61B 18/14*    (2006.01)
*A61B 17/32*    (2006.01)
(Continued)

(52) U.S. Cl.
CPC ..... *A61B 18/1402* (2013.01); *A61B 17/32002* (2013.01); *A61B 2017/00464* (2013.01);
(Continued)

(58) Field of Classification Search
CPC .............. A61B 2018/0091; A61B 2017/0046; A61B 2017/00464
See application file for complete search history.

(56) References Cited

U.S. PATENT DOCUMENTS

| 1,814,791 A | 7/1931 | Ende |
| 1,952,617 A | 3/1934 | Wappler |

(Continued)

FOREIGN PATENT DOCUMENTS

| CN | 1130052 A | 9/1996 |
| CN | 1655728 A | 8/2005 |

(Continued)

OTHER PUBLICATIONS

Trident® The Power of Three, webpage from http://www.conmed.com/products, ConMed Linvatec—Arthroscopy—ESA—Trident™ (2001).
ConMed's Linvatec Subsidiary Announces the Release of the Trident (TM) Resection Ablator, 2 pages, Apr. 19-22, 2001.
Smith & Nephew, Dyonics Electroblade, webpage from http://global.smith-nephew.com (2005).
(Continued)

*Primary Examiner* — Joseph Stoklosa
*Assistant Examiner* — Nicole L Pobre
(74) *Attorney, Agent, or Firm* — Flynn, Thiel, Boutell & Tanis, P.C.

(57) ABSTRACT

A surgical tool arrangement a handpiece which is capable of accepting and operating a number of different surgical tools or instruments adapted for use with the handpiece, each having one or multiple functions. The handpiece incorporates a coupling arrangement located at a distal end thereof which serves to attach the desired surgical instrument to the hand-piece via a locking mechanism, and also provides an electrical contact arrangement to support the functioning of an electrosurgical probe as well as a combined mechanical cutting and electrosurgical tool. Additionally, the handpiece accepts a conventional cutter which only requires power for driving a movable cutting element.

27 Claims, 26 Drawing Sheets

(51) Int. Cl.
*A61B 17/00* (2006.01)
*A61B 18/00* (2006.01)

(52) U.S. Cl.
CPC ............ *A61B2018/0063* (2013.01); *A61B 2018/00577* (2013.01); *A61B 2018/00589* (2013.01); *A61B 2018/00595* (2013.01)

(56) References Cited

U.S. PATENT DOCUMENTS

| | | | |
|---|---|---|---|
| 2,056,377 A | 10/1936 | Wappler | |
| 2,275,167 A | 3/1942 | Bierman | |
| 3,746,814 A | 7/1973 | Lackey et al. | |
| 3,945,375 A | 3/1976 | Banko | |
| 4,034,761 A | 7/1977 | Prater et al. | |
| 4,232,676 A | 11/1980 | Herczog | |
| 4,301,802 A | 11/1981 | Poler | |
| 4,700,997 A | 10/1987 | Strand | |
| 4,815,462 A | 3/1989 | Clark | |
| 4,850,354 A | 7/1989 | McGurk-Burleson et al. | |
| 4,998,527 A | 3/1991 | Meyer | |
| 5,084,045 A | 1/1992 | Helenowski | |
| 5,192,292 A | 3/1993 | Cezana et al. | |
| 5,217,478 A | 6/1993 | Rexroth | |
| 5,217,479 A | 6/1993 | Shuler | |
| 5,254,117 A | 10/1993 | Rigby et al. | |
| 5,277,696 A | 1/1994 | Hagen | |
| 5,364,395 A | 11/1994 | West, Jr. | |
| 5,413,575 A | 5/1995 | Haenggi | |
| 5,429,596 A | 7/1995 | Arias et al. | |
| 5,492,527 A | 2/1996 | Glowa et al. | |
| 5,527,331 A | 6/1996 | Kresch et al. | |
| 5,607,391 A * | 3/1997 | Klinger et al. | 604/33 |
| 5,609,573 A | 3/1997 | Sandock | |
| 5,782,795 A | 7/1998 | Bays | |
| 5,810,809 A | 9/1998 | Rydell | |
| 5,827,279 A | 10/1998 | Hughett et al. | |
| 5,860,975 A | 1/1999 | Goble et al. | |
| 5,904,681 A | 5/1999 | West, Jr. | |
| 5,925,045 A | 7/1999 | Reimels et al. | |
| 5,941,876 A | 8/1999 | Nardella et al. | |
| 6,004,320 A | 12/1999 | Casscells et al. | |
| 6,007,533 A | 12/1999 | Casscells et al. | |
| 6,149,646 A | 11/2000 | West, Jr. et al. | |
| 6,193,715 B1 | 2/2001 | Wrublewski et al. | |
| 6,214,001 B1 | 4/2001 | Casscells et al. | |
| 6,312,441 B1 | 11/2001 | Deng | |
| 6,464,512 B2 | 10/2002 | Morita | |
| 6,485,436 B1 | 11/2002 | Truckai et al. | |
| 6,610,059 B1 | 8/2003 | West, Jr. | |
| 6,663,628 B2 | 12/2003 | Peters | |
| 6,692,516 B2 | 2/2004 | West, Jr. et al. | |
| 6,827,725 B2 | 12/2004 | Batchelor et al. | |
| 6,837,888 B2 | 1/2005 | Ciarrocca et al. | |
| 6,840,937 B2 | 1/2005 | Van Wyk | |
| 6,918,906 B2 | 7/2005 | Long | |
| 6,979,332 B2 | 12/2005 | Adams | |
| 7,052,494 B2 | 5/2006 | Goble et al. | |
| 7,060,063 B2 | 6/2006 | Marion et al. | |
| 7,150,747 B1 | 12/2006 | McDonald et al. | |
| 7,226,460 B2 | 6/2007 | Gibson et al. | |
| 7,452,358 B2 | 11/2008 | Stern et al. | |
| 2003/0060862 A1 | 3/2003 | Goble et al. | |
| 2003/0135151 A1 | 7/2003 | Deng | |
| 2004/0078037 A1 | 4/2004 | Batchelor et al. | |
| 2004/0220602 A1 | 11/2004 | Deng et al. | |
| 2005/0080412 A1 | 4/2005 | Ouchi | |
| 2005/0107779 A1 | 5/2005 | Ellman et al. | |
| 2005/0228374 A1 | 10/2005 | Desinger et al. | |
| 2006/0200123 A1 | 9/2006 | Ryan | |
| 2006/0235377 A1 | 10/2006 | Earley et al. | |
| 2006/0264927 A1 | 11/2006 | Ryan | |
| 2007/0016185 A1* | 1/2007 | Tullis | A61B 18/1477 606/41 |
| 2008/0058802 A1 | 3/2008 | Couture et al. | |
| 2008/0188848 A1 | 8/2008 | Deutmeyer et al. | |
| 2009/0299366 A1 | 12/2009 | Desinger et al. | |
| 2009/0306656 A1 | 12/2009 | Desinger et al. | |
| 2011/0301578 A1 | 12/2011 | Muniz-Medina et al. | |

FOREIGN PATENT DOCUMENTS

| | | | |
|---|---|---|---|
| CN | 1780588 A | 5/2006 | |
| CN | 2868225 Y | 2/2007 | |
| CN | 102333490 A | 1/2012 | |
| DE | 196 41 564 C1 | 10/1996 | |
| JP | 03143437 A2 | 6/1991 | |
| JP | 2005-536272 A | 12/2005 | |
| JP | 2008-532712 A | 8/2008 | |
| WO | WO 85/00280 | 1/1985 | |
| WO | WO 90/07303 | 7/1990 | |
| WO | WO 97/24073 A1 | 7/1997 | |
| WO | WO 97/33523 | 9/1997 | |
| WO | WO 98/03117 | 1/1998 | |
| WO | WO 99/13788 | 3/1999 | |
| WO | WO 2004/017849 A1 | 3/2004 | |
| WO | WO 2006/102124 A2 | 9/2006 | |
| WO | WO 2006102124 A2 * | 9/2006 | ............ A61B 17/32 |
| WO | WO 2010/098809 A2 | 9/2010 | |

OTHER PUBLICATIONS

Coagulating Arthroscopy Shaver: A New Device, Vahan A. Kilaghbian, M.D., (7 pages) (1996).
International Preliminary Report on Patentability and Written Opinion from corresponding International Appln. No. PCT/US2010/000202, issued Aug. 30, 2011, 11 sheets.
International Search Report and Written Opinion for corresponding PCT Application No. PCT/US2010/000202.
Office Action of Japanese Patent Office dated Sep. 13, 2013 with English translation issued in Japanese Application No. 2011-552019 (7 pages).
Chinese Office Action and Search Report issued in Appln. No. 201410098133.7 with English translation dated Jul. 3, 2015 (16 pages).
European Office Action issued in Appln. No. 06738812.4 dated Dec. 23, 2010 (4 pages).
Japanese Office Action issued in Appln. No. 2008-502112 dated Aug. 22, 2011 with English Translation (7 pages).
Japanese Office Action issued in Appln. No. 2008-502112 dated Feb. 20, 2012 with English Translation (7 pages).
United States Restriction Requirement issued in U.S. Appl. No. 11/886,393 dated Mar. 19, 2012 (6 pages).
United States Office Action issued in U.S. Appl. No. 11/886,393 dated May 4, 2012 (23 pages).
United States Final Office Action issued in U.S. Appl. No. 11/886,393 dated Dec. 20, 2012 (26 pages).
Australian Examination Report issued in Appln. No. 2010218473 dated Jan. 23, 2013 (4 pages).
European Office Action issued in Appln. No. 06738812.4 dated Feb. 1, 2013 (3 pages).
Chinese Office Action issued in Appln. No. 201080009460.0 dated May 27, 2013 with English Translation (11 pages).
Australian Examination Report issued in Appln. No. 2010218473 dated Jun. 3, 2013 (3 pages).
European Office Action issued in Appln. No. 06738812.4 dated May 6, 2014 (3 pages).
European Office Action issued in Appln. No. 10706804.1 dated Sep. 22, 2014 (4 pages).
United States Office Action issued in U.S. Appl. No. 11/886,393 dated Mar. 4, 2015 (20 pages).
Chinese Office Action issued in Appln. No. 201410098130.3 dated Jul. 31, 2015 with English Translation (8 pages).
United States Final Office Action issued in U.S. Appl. No. 11/886,393 dated Aug. 12, 2015 (19 pages).
United States Advisory Action issued in U.S. Appl. No. 11/886,393 dated Nov. 3, 2015 (4 pages).

* cited by examiner

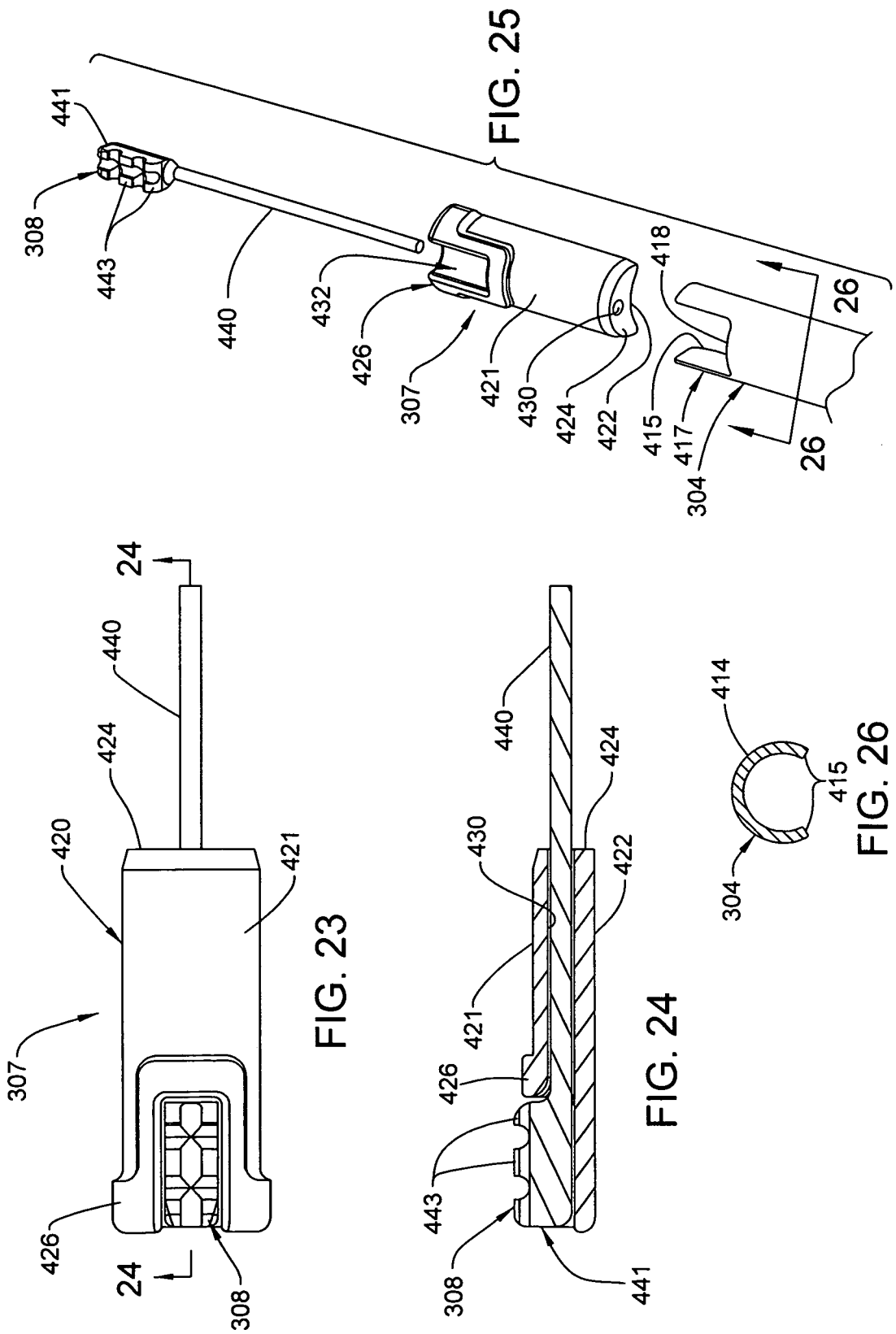

SURGICAL TOOL ARRANGEMENT HAVING A HANDPIECE USABLE WITH MULTIPLE SURGICAL TOOLS

CROSS REFERENCE TO RELATED APPLICATION

This application is the National Stage of International Application No. PCT/US2010/000202, filed Jan. 25, 2010, which claims the benefit of U.S. Provisional Application Ser. No. 61/208,637, filed Feb. 26, 2009, which is incorporated herein by reference in its entirety.

FIELD OF THE INVENTION

This invention generally relates to a powered surgical tool arrangement useful for performing endoscopic surgical procedures and, more particularly, to a system with a handpiece which is able to operate a number of different surgical tools or instruments which detachably connect to the handpiece.

BACKGROUND OF THE INVENTION

Endoscopic surgical procedures are routinely performed in order to accomplish various surgical tasks. In such a surgical procedure, small incisions or portals are made in the patient. An endoscope, which is a device that allows medical personnel to view the surgical site, is inserted in one of the portals. Surgical instruments used to perform other tasks are inserted into other portals. The surgeon views the surgical site through the endoscope to determine how to manipulate the surgical instruments in order to accomplish the desired procedure. An advantage of performing endoscopic surgery is that, since the portions of the body that are cut open are minimized, the portions of the body that need to heal after the surgery are likewise reduced. Moreover, during an endoscopic surgical procedure, only relatively small portions of the patient's internal organs and tissue are exposed to the open environment. This minimal opening of the patient's body lessens the extent to which a patient's organs and tissue are open to infection.

The ability to perform endoscopic surgery is enhanced by the development of powered surgical tools especially designed to perform such procedures. Once such tool is sold by the Assignee hereof under the trademark FORMULA®. This tool is in the form of a cylindrical handpiece designed to be held in the hand of the surgeon. The handpiece has a front or distal end provided with a coupling assembly for releasably holding a cutting tool or instrument, and a motor disposed within a handpiece housing. Such cutting tools include mechanical cutting instruments in the form of shavers and burrs. These tools include an outer cannula having a proximal end which is fixed to a hub, and a drive shaft disposed within and movable relative to the outer cannula. The tool hub is appropriately configured to cooperate with the coupling assembly of the handpiece to lock the tool thereto. When the selected tool is attached to the handpiece, the handpiece motor couples to the drive shaft of the tool. The handpiece motor is selectively actuable to drive the tool drive shaft so as to cause a desired cutting action at the distal end of the tool. The handpiece is associated with a control unit which controls the functioning thereof, and is actuated by the user via appropriate buttons provided on the handpiece itself, or alternatively directly at the control unit.

In an endoscopic surgical procedure, irrigating fluid is introduced into the surgical site. This fluid serves as a transport media for removing tissue and debris from the surgical site. In order to remove the irrigating fluid and the material contained therein, the above handpiece and the various tools which are usable therewith together define a suction conduit. A suction pump is connected to the handpiece to provide the suction force needed for drawing the fluid and material away from the surgical site. In order to control the suction flow through the tool and the handpiece, the handpiece is provided with a manually operated valve. Thus, the surgeon is able to manipulate the surgical tool and control suction of material away from the surgical site.

Tools other than the handpiece and the associated cutting tools described above may be used during a surgical procedure. One such tool is an electrosurgical probe or radiofrequency (RF) probe. This probe utilizes electrical energy to treat patient tissue in various ways. For example, electrocauterization is utilized to seal off and close blood vessels during surgery to prevent blood loss. In addition, ablation is utilized to vaporize or remove tissue using electrical energy. Electrosurgical probes are typically designed to perform both of these functions, depending upon the level of power supplied thereto. Further, monopolar and bipolar electrosurgical tools are conventional wherein monopolar tools direct electric current from an active electrode defined on the tool through the patient's body to a return electrode, which return electrode is typically defined by a grounding pad attached to the patient. Bipolar tools, on the other hand, include both an active and return electrode, wherein the current is directed from the active electrode to the return electrode through the contacted tissue. Such electrosurgical tools are controlled through a console or control unit which delivers appropriate power levels to the tool to perform the desired procedure on the patient.

Another type of surgical tool is one which combines the mechanical cutting action of a shaver or burr and the electrosurgical treatment of tissue via an electrode. This tool typically incorporates a movable blade which is actuated for mechanical cutting, as well as either a monopolar or bipolar electrode arrangement at the distal end of the tool. This combination-type tool thus eliminates the user having to handle two separate tools, one for electrosurgical procedures and another for cutting procedures.

While the above-described handpiece arrangement and various tools have proven useful, same can require the purchase of wholly separate systems, each having its own control unit, which can result in greater costs and a greater number of surgical tools which must be present in order to carry out the desired procedure. Operation of these separate tools can also be taxing on the surgeon or surgical staff.

In order to obviate or at least minimize the above disadvantages of known arrangements, the surgical tool arrangement according to the invention provides a handpiece which is usable with a variety of types of surgical instruments which are all adapted for use with the handpiece, meaning that one handpiece is usable for a multitude of surgical procedures.

Specifically, the handpiece according to the invention incorporates a coupling member located at a distal end thereof which serves to attach the desired surgical tool to the handpiece, and also provides an electrical contact arrangement to effectively support the functioning of an electrosurgical probe as well as a combined mechanical cutting and electrosurgical tool. Additionally, the handpiece is capable of accepting a conventional cutter or shaver which simply requires power for driving its movable cutting element.

The handpiece according to the invention additionally incorporates therein a locking arrangement including a release lever mounted on the distal end of the handpiece. The locking arrangement is configured such that no manipulation thereof is necessary to allow attachment and locking of the surgical tool to the handpiece. The release lever is movable to a release position to unlock the surgical tool and allow removal of same from the handpiece.

BRIEF DESCRIPTION OF THE DRAWINGS

FIG. 23 is an enlarged plan view of the electrode assembly of the tool of FIG. 12;

FIG. 24 is an enlarged cross-sectional view of the electrode assembly of FIG. 23, taken generally along line 24-24 in FIG. 23;

FIG. 25 is an enlarged, exploded and fragmentary perspective view of the electrode assembly and barrel of the tube assembly of the tool of FIG. 12;

FIG. 26 is an enlarged cross-sectional view of the barrel of the tube assembly, as seen generally along line 26-26 in FIG. 25;

Figure 1:
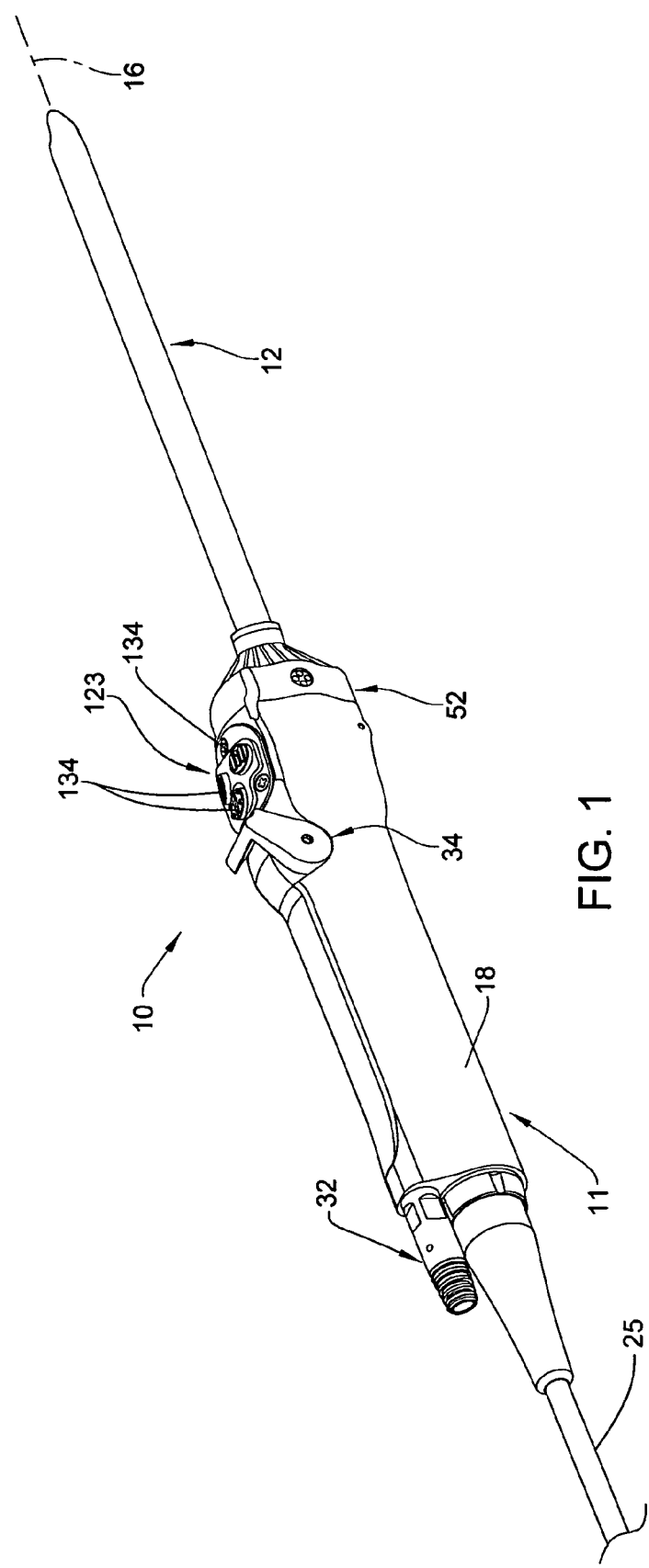
FIG. 1 is a perspective view of the surgical tool arrangement according to the invention, including a handpiece with a surgical tool attached thereto.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

Figure 2:
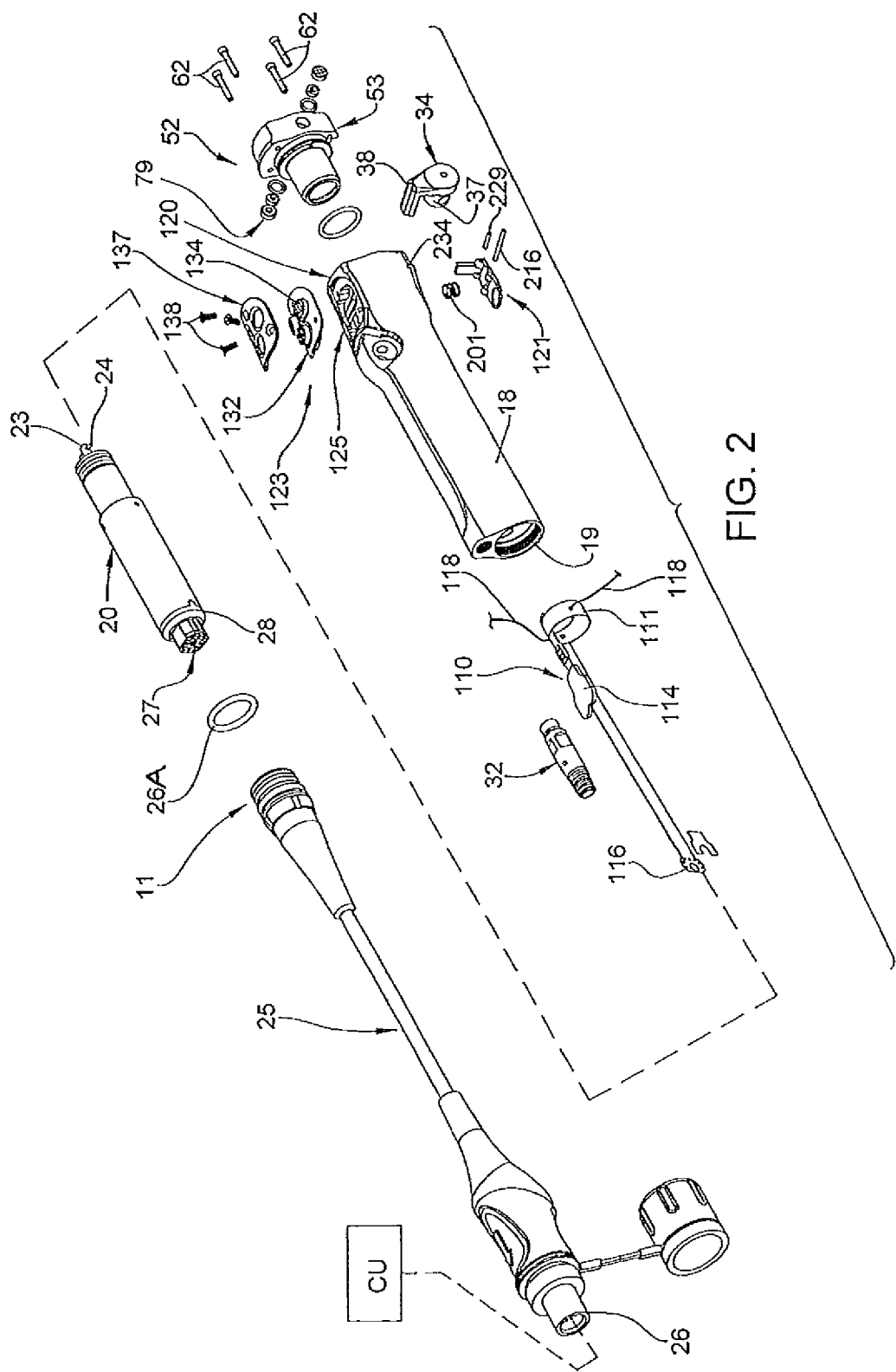
FIG. 2 is an exploded view of the handpiece of FIG. 1.
Figure 3:
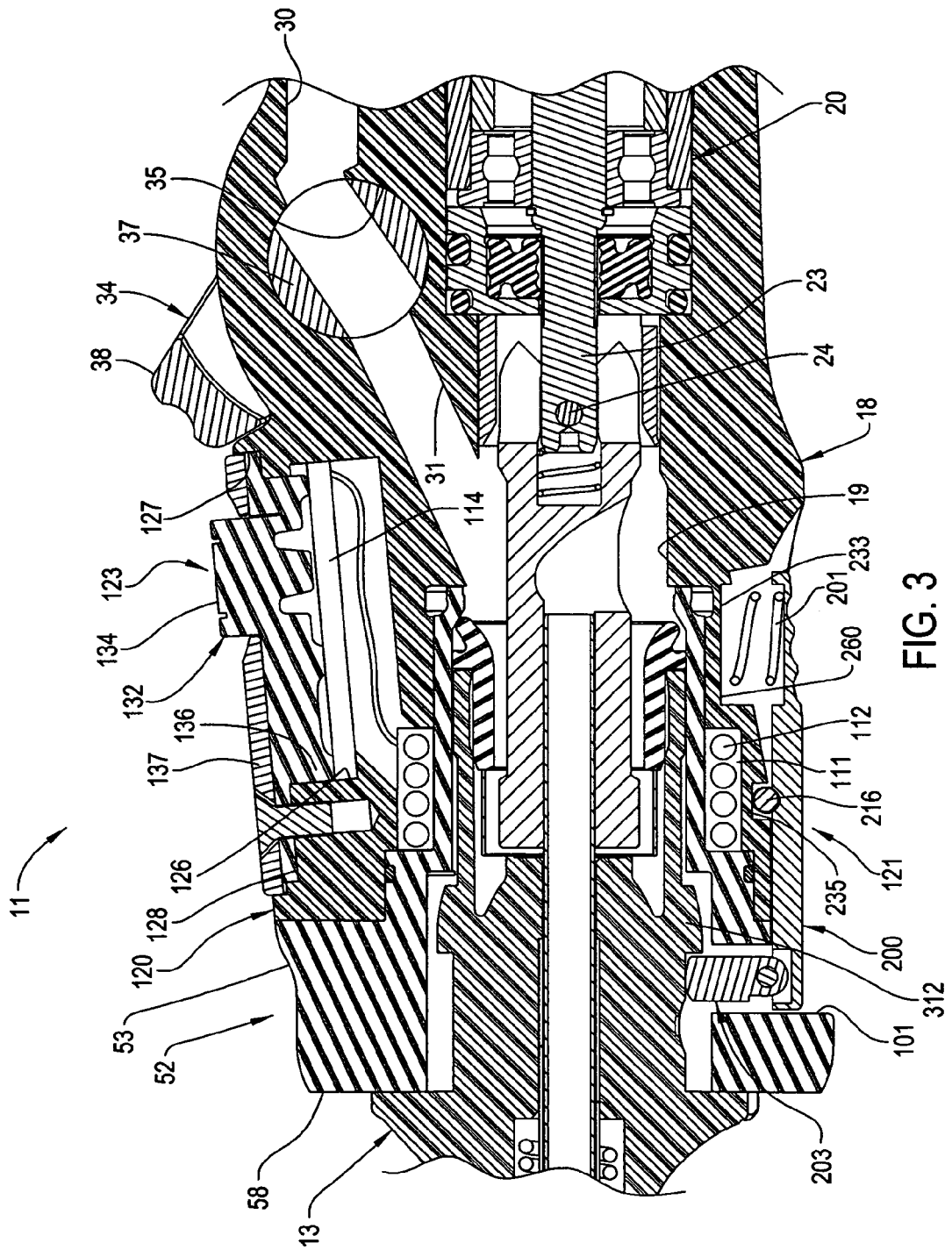
FIG. 3 is an enlarged, fragmentary longitudinal cross-sectional view of the handpiece of FIG. 1 with a surgical tool attached thereto.

Referring to FIGS. 1-3, a surgical tool arrangement 10 according to the invention is illustrated. The arrangement 10 includes a handpiece 11, which at a distal end mounts thereon a surgical tool or instrument 12. In this regard, the tool 12 shown in FIG. 1 may be one of a variety of tools which can be utilized with handpiece 11. Specifically, the handpiece 11 is configured for selectively attaching to, and supporting the functionality of, multiple surgical tools or instruments, such as a combined electrosurgical and mechanical cutting instrument 13, a surgical cutter or shaver 14 and an electrosurgical instrument or probe 15. The structure and functioning of all of instruments 13, 14 and 15 are discussed further below.

Handpiece 11 defines a generally central longitudinal axis 16, and includes an elongate and generally cylindrical housing 18 defining an elongate bore 19 therein. A motor 20 is disposed within housing bore 19, and includes an output or drive shaft 23. Drive shaft 23 mounts a drive pin 24 at the distal end thereof. A cable 25 is coupled to the proximal end of handpiece 11, and includes a connector 26 at the proximal end which interfaces with a control unit (CU). Control unit (CU) controls motor 20 of handpiece 11 to provide driving power to the instruments 13 and 14, and also serves as a radio-frequency (RF) generator to power electrodes of instruments 13 and 15. The distal end of cable 25 interfaces with an electrical connector 27 provided at the proximal end of motor 20. A seal 26A is interposed between the distal end of cable 25 and connector 27. The proximal end of motor 20 includes a cap 28 which is openable to allow connection of circuitry (described further below) to connector 27.

Handpiece housing 18 defines therein an elongate suction bore 30 extending generally parallel to and sidewardly of housing bore 19. Suction bore 30 communicates with a diagonally extending suction passage 31 defined in housing 18, which passage 31 provides communication between the proximal end of housing bore 19 and the suction bore 30. Suction is drawn through the handpiece 11 by a suction pump (not shown), which is connected to the handpiece 11 via a fitting 32 which connects to a suction tube (not shown). Fitting 32 is mounted in the proximal end of housing 18. Suction flow through the handpiece 11 is regulated by an adjustable valve 34 mounted to housing 18. More particularly, valve 34 is rotatably mounted in a valve bore 35 formed in housing 18, and includes a valve stem 37 rotatably seated in valve bore 35 and an arm or handle 38. Arm 38 is the exposed portion of the valve 34 that is manually set by the user to position the valve stem 37 at the desired position within housing bore 35. The above handpiece suction arrangement is described in U.S. Patent Application Publication No. 2003/0135151A1 published on Jul. 17, 2003, which is owned by the same assignee hereof and is hereby incorporated by reference herein.

The tools or instruments 13, 14 and 15 are individually and removably attached to the distal end of handpiece 11 by a coupling assembly 52 provided on the handpiece 11. As shown in FIGS. 4-7, coupling assembly 52 includes a collet 53 secured to the distal end of handpiece housing 18. Collet 53 defines a generally ring-shaped distal end 55 which defines the distal end of handpiece 11 and receives therein one of tools 13, 14 or 15, and a generally tubular neck 56. Neck 56 is fixed to, and projects proximally or rearwardly from, distal end 55 of collet 53. Neck 56 has an outer diameter which is significantly less than an outer diameter of distal end 55.

Distal end 55 of coupling assembly 52 has a front or distal face 58 and a rear or proximal face 59 which are generally parallel to one another. A plurality of bores 60, and here four, extend through distal end 55 between the front and rear faces 58 and 59, in which respective fasteners 62 (see FIG. 2) are disposed in order to connect the collet 53 to the distal end of handpiece housing 18 as discussed below.

Collet 53 defines therein a central bore 64 which extends through the entire axial extent thereof so as to open distally through front face 58 and proximally through neck 56. Central bore 64 is located radially inwardly of bores 60. Additionally, a pair of elongated channels 66 are defined in an inner annular surface 65 of collet 53 which defines bore 64. More particularly, channels 66 are located diametrically opposite one another within bore 64 of collet 53, with one of the channels 66 being located circumferentially between the respective bores of the upper pair of bores 60, and the other channel 66 being located circumferentially between the respective bores of the lower pair of bores 60. A further pair of channels 67 are located diametrically opposite one another within bore 64, and are approximately 90 degrees offset from the channels 67. The portion of annular surface 65 of collet 53 in which the channels 67 are disposed is generally ramp-shaped, such that surface 65, at channels 67, diverges gradually outwardly in the proximal to distal direction. Channels 66 and 67 all open through distal face 58 of collet 53.

Distal end 55 of collet 53 has a pair of outer side surfaces 68 and top and bottom surfaces 69 and 70, all of which surfaces extend axially between and interconnect front and rear faces 58 and 59. Further, a pair of bores 73 extend radially through distal end 55. More particularly, bores 73 are oriented diametrically opposite one another along the outer peripheral surface (collectively defined by surfaces 68, 69 and 70) of collet 53 adjacent the respective channels 67. Bores 73 extend radially from the respective side surfaces 68 and open into collet bore 64 through inner surface 65. Further, bores 73 have threaded outer ends 74 which are generally cylindrical in shape and respective inwardly-oriented counter bores 75 having inner reduced-diameter ends 76 which open into the respective channels 67.

Figure 4:
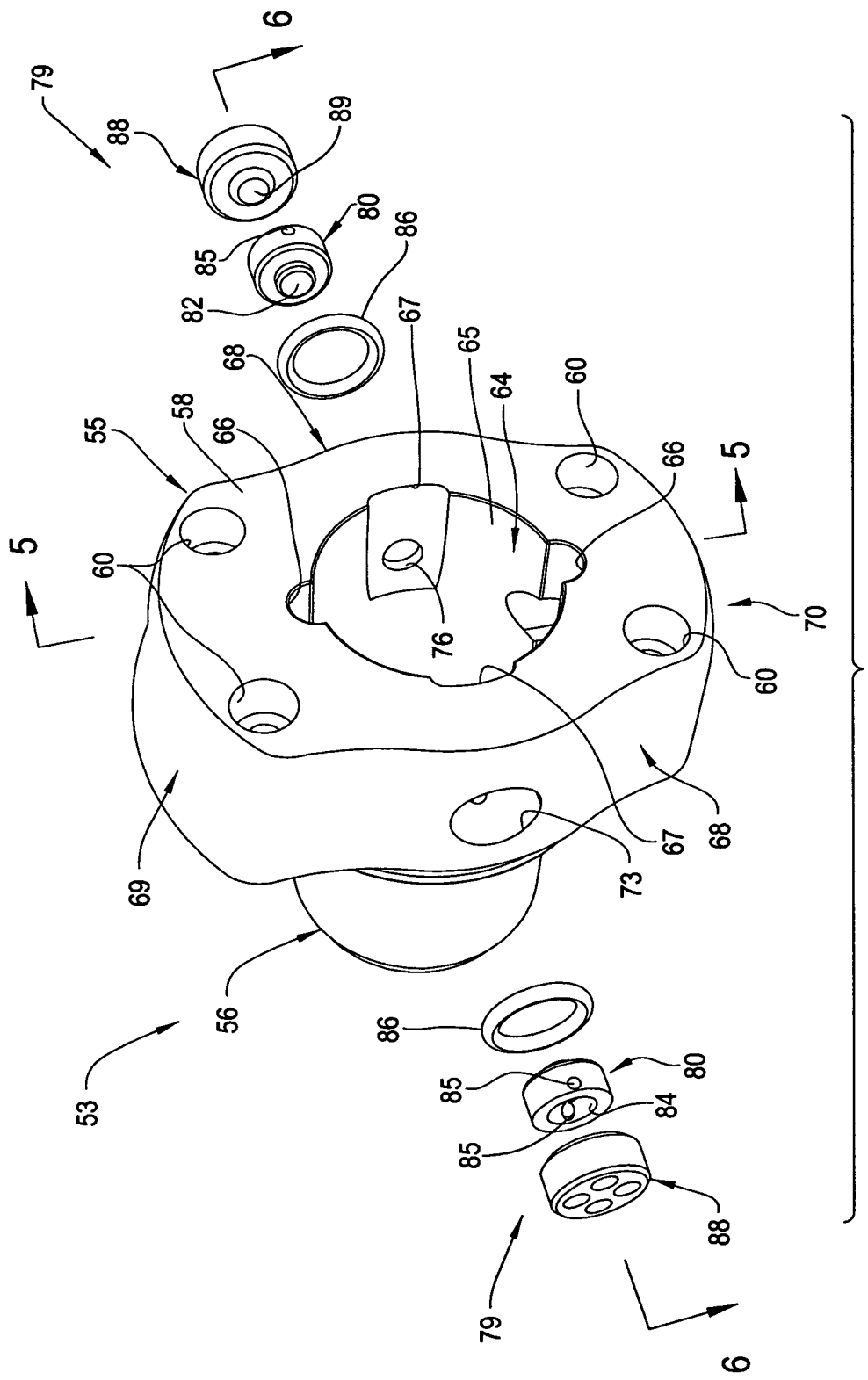
FIG. 4 is an enlarged and exploded perspective view of the coupler of the handpiece of FIG. 1.

As shown in FIG. 4, distal end 55 of collet 53 mounts thereon a pair of identical contact arrangements 79, and only one of which will accordingly be described. Contact arrangement 79 includes a button-like contact 80. Contact 80 is generally cylindrical and has an inner surface with a generally circular projection 82 thereon, which projection 82 is shaped to seat within the respective inner end 76 of bore 73. An outer surface of contact 80 defines therein a radially-inwardly projecting recess 84, and a pair of wire-receiving openings 85 are defined in a peripheral side surface of contact 80.

Contact arrangement 79 additionally includes a seal 86 in the form of an O-ring which seats in counterbore 75 of bore 73, and a cap 88 which is threaded exteriorly so as to engage within the threaded outer end 74 of the respective bore 73. Cap 88 also includes a centering projection 89 located on an inner end thereof which is configured to seat in recess 84 of contact 80.

Collet 53 additionally includes an annular stepped portion 92 disposed axially between and adjoining distal end 55 and neck 56. Stepped portion 92 is of a slightly greater outer diameter than neck 56, and defines therein a pair of wiring channels 93 diametrically opposite one another along stepped portion 92. Wiring channels 93 extend axially from a rearward or proximally-facing surface 94 of portion 92 to the respective bores 73 so as to communicate with same. Stepped portion 92 also defines therein a radially outwardly opening and circumferentially extending channel 95 along the outer surface thereof in which an O-ring 97 is disposed.

Figure 5:
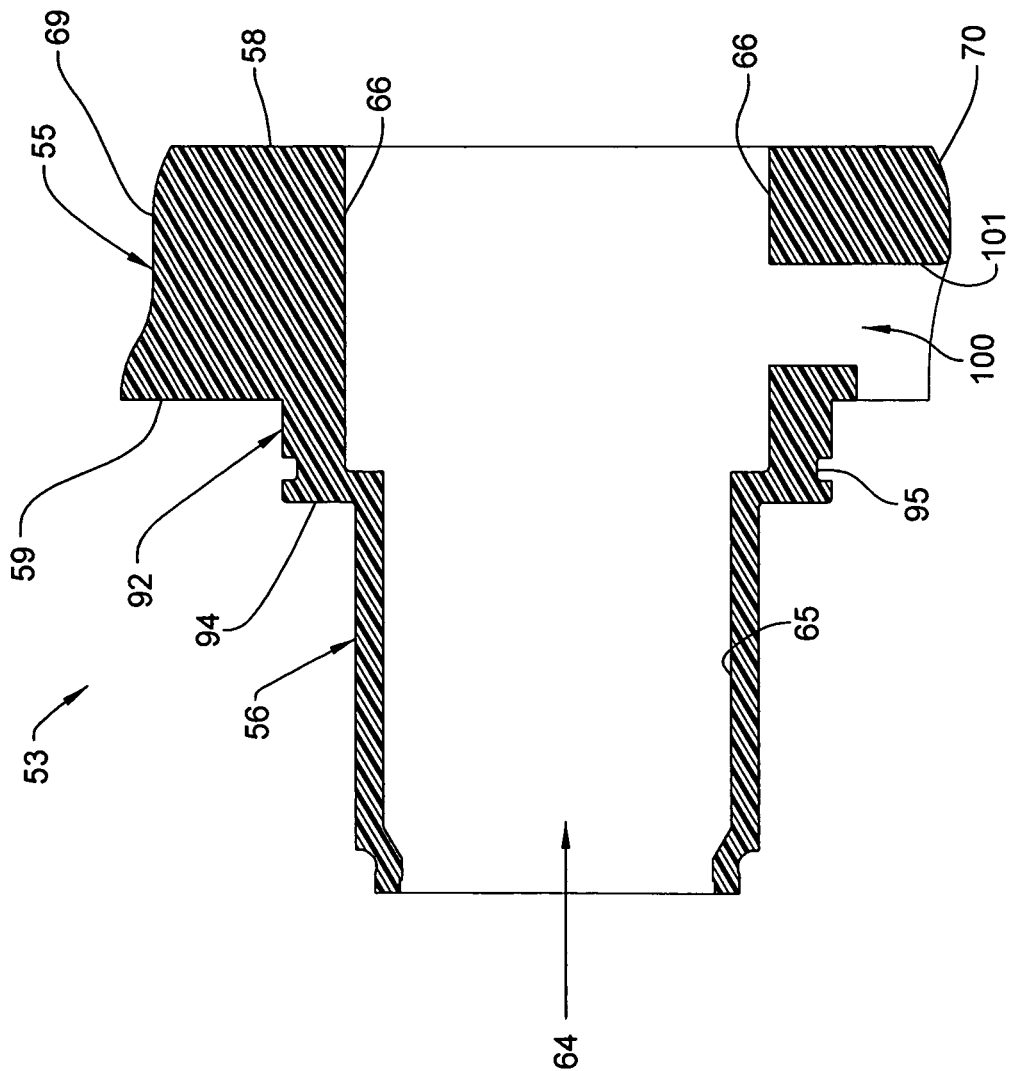
FIG. 5 is an enlarged cross-sectional view of the coupler of FIG. 4, as seen generally along line 5-5 in FIG. 4.
Figure 7:
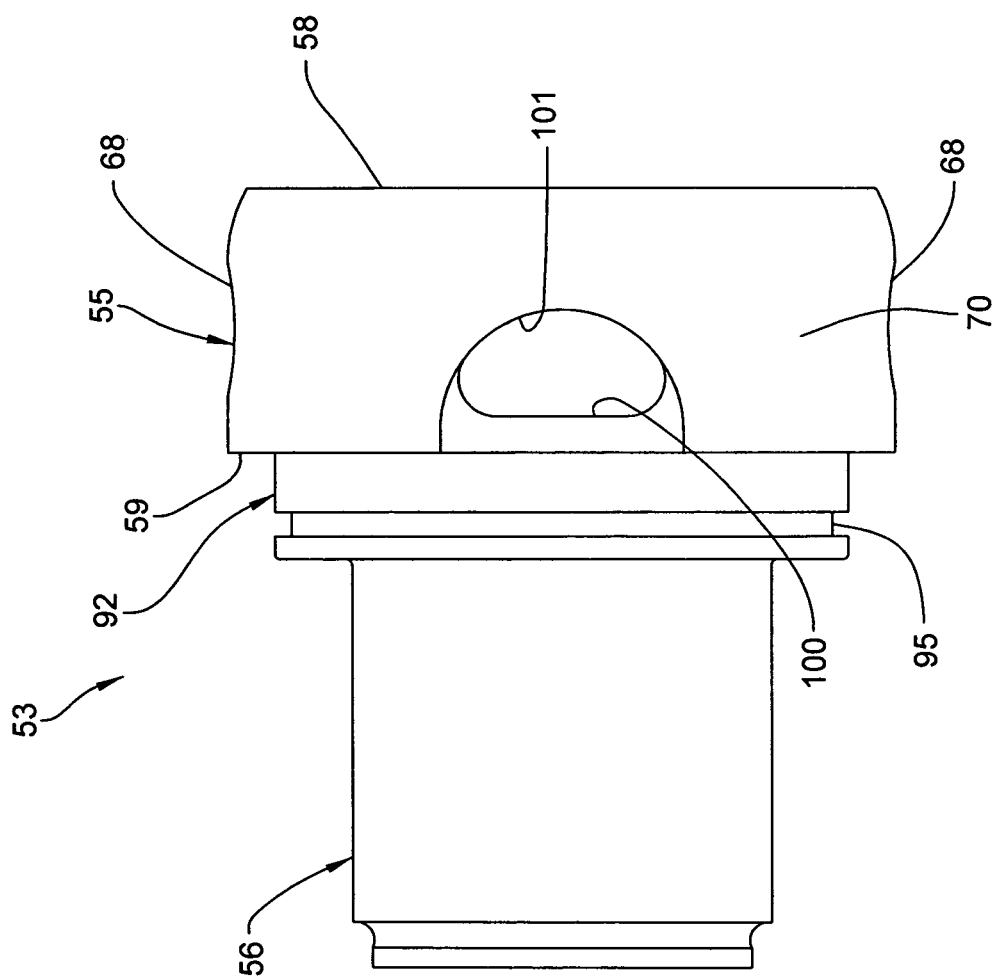
FIG. 7 is an enlarged bottom view of the coupler of FIG. 4.

As shown in FIGS. 5 and 7, the lower portion of distal end 55 of collet 53 defines therein a vertically-oriented channel 100 which opens inwardly into collet bore 64 and outwardly through a semi-circular opening 101 located at bottom surface 70 of distal end 55.

Referring to FIGS. 2 and 3, collet 53 mounts thereon a flexible circuit assembly 110 having a distal end in the form of a loop 111 sized to fit over the neck 56 of collet 53. A coil 112 is provided on loop 111, and a membrane switch 114 is connected to loop 111. Coil 112 is used to facilitate inductive signal transfer to/from a radio-frequency identification device (RFID) disposed in each of the respective instruments 13, 14 and 15. Circuit assembly 110 additionally includes a tab 116 which defines the proximal end thereof and connects to connector 27 of motor 20.

Each contact arrangement 79 is assembled to collet 53 by inserting O-ring 86 into bore 73 and seating same in counterbore 75 thereof. Contact 80 is then inserted into bore 73 so that the projection 82 projects into inner end or opening 76 of bore 73. When contact 80 is installed in bore 73, as discussed above, one of the openings 85 aligns with a channel 93 of collet 53. Cap 88 is then threaded into outer portion 74 of bore 73. As cap 88 is installed in bore portion 74, the centering projection 89 engages in recess 84 of contact 80 which ensures proper alignment. Flexible circuit assembly 110 is then assembled to collet 53 by sliding the loop end 111 over neck 56, and electrically connecting end 111 to the respective contacts 80 via wires 118 (FIG. 2)

which extend from end 111, into the respective channels 93 of stepped portion 92, and into openings 85 of the respective contacts 80.

With reference to FIGS. 1, 2, 3 and 8, handpiece housing 18 at a distal end 120 thereof (through which bore 19 opens) mounts thereon a locking assembly 121 and a control arrangement 123 located diametrically opposite one another on housing 18. As discussed further below, locking assembly 121 forms part of coupling assembly 52. Handpiece housing 18 defines therein an upwardly-opening recess 125 in which control arrangement 123 is mounted, and which opens at its inner end into housing bore 19. Recess 125 is defined by a generally upright and annular lower housing wall 126, and a generally upright and annular upper housing wall 127. Upper housing wall 127 is offset outwardly from lower housing wall 126 by an annular step surface 128 which extends transversely between and interconnects housing walls 126 and 127.

Control arrangement 123 includes a keypad 132 having an upper portion which defines thereon a plurality, and here three, of buttons 134, and a lower portion 136 which projects downwardly from upper portion 133. Arrangement 123 further includes a switchplate or cover 137.

With flexible circuit assembly 110 and contact arrangements 79 assembled to collet 53 as discussed above, collet 53 is assembled to distal end 120 of handpiece housing 18 by inserting the proximal end of flexible circuit 110 and neck 56 of collet 53 into housing bore 19 at distal end 120. Collet 53 is advanced proximally relative to housing 18 until the rear face 59 of distal end 55 abuts distal end 120. The membrane switch 114 of circuit assembly 110 is inserted up into housing recess 125 from bore 19 and seated against lower housing wall 126. Membrane switch 114 is then flipped over from the orientation shown in FIG. 2 and positioned in recess 125 and seated against housing wall 126. The elongated portion of circuit assembly 110 which extends proximally from loop 111 extends proximally within housing bore 19 along the exterior of motor 20. Keypad 132 is then positioned atop membrane switch 114 within recess 125. In this regard, as shown in FIGS. 2 and 3, housing wall 126 is shaped so as to correspond to both the outer periphery of membrane switch 114 and the outer periphery of lower portion 136 of keypad 132 positioned atop switch 114. Switchplate 137 is then positioned atop keypad 132 and fastened to handpiece housing 18 via fasteners 138 which extend downwardly through switchplate 137 and into corresponding threaded bores defined in housing 18. Fasteners 62 can then be inserted through the respective openings 60 of collet 53 and into corresponding threaded bores defined in the end face of distal end 120 of housing 18.

Flexible circuit assembly 110 electrically connects contact arrangements 79 of collet 53 and control arrangement 123 to control unit (CU). Specifically, tab 116 of flexible circuit 110 is connected to connector 27 of motor 20 by opening cap 28 at the proximal end of motor 20 and seating tab 116 under connector 27 so that tab 116 is positioned between connector 27 and cap 28, which effectively electrically connects the control arrangement 123 and contact arrangements 79 to the appropriate wires located within cable 25.

Turning now to locking assembly 121, and with reference to FIGS. 3 and 8-11, same includes an elongate lock lever or arm 200, a spring 201 and a slider bar 203. Lock lever 200 has a distal end 204 mounting thereon a hinge 205 which cooperates with slider bar 203. Hinge 205 includes a pair of spaced-apart mounting elements 206, each of which defines an opening 207 therethrough which is elongated in the axial direction. An upwardly-opening recessed area 208 is defined between mounting elements 206. A proximal end 210 of lock lever 200 on a lower side thereof defines an undulated gripping surface 211, and on an upper side thereof defines an inwardly-projecting and generally circular recess 212. A pair of spaced-apart mounting elements 215 are located approximately mid-way between proximal and distal ends 210 and 204 of lock lever 200, which elements 215 are configured to receive therethrough a pivot pin 216 for pivotably mounting locking assembly 121 to handpiece 11.

Slider bar 203 has an upper terminal end 220 defining a rounded surface 221, and a lower terminal end or foot 225 which is sized to seat between the respective mounting elements 206 of lock lever 200 and defines therein a through bore 228. The lower surface of foot 225 is of an arcuate or convex shape. Slider bar 203 is mounted to lock lever 200 by inserting foot 225 between mounting elements 206 so that the lower surface of foot 225 is disposed within recessed area 208, and inserting a pivot pin 229 into one mounting element 206, through bore 228 in foot 225 and into the opposite mounting element 206.

Figure 8:
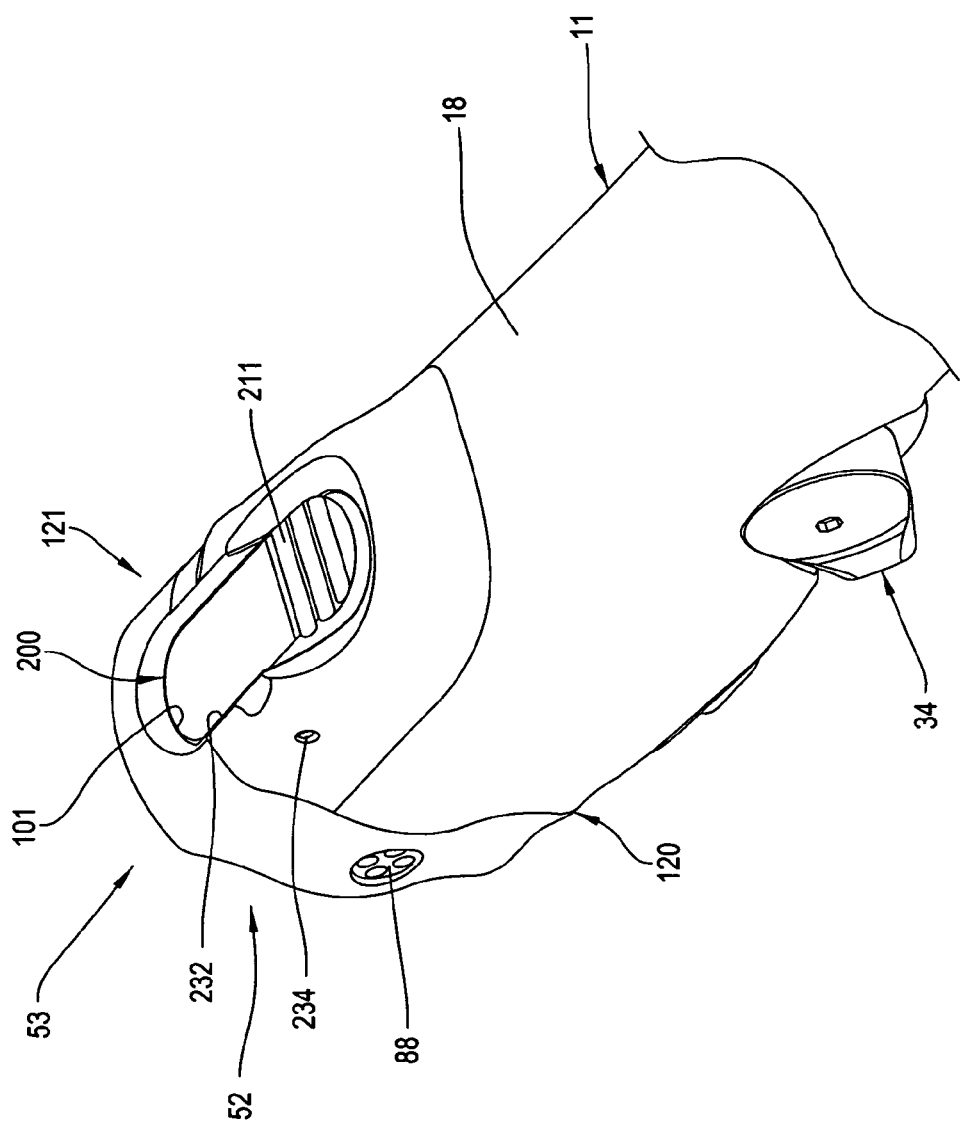
FIG. 8 is an enlarged and fragmentary view of the coupling arrangement of the handpiece of FIG. 1.
Figure 9:
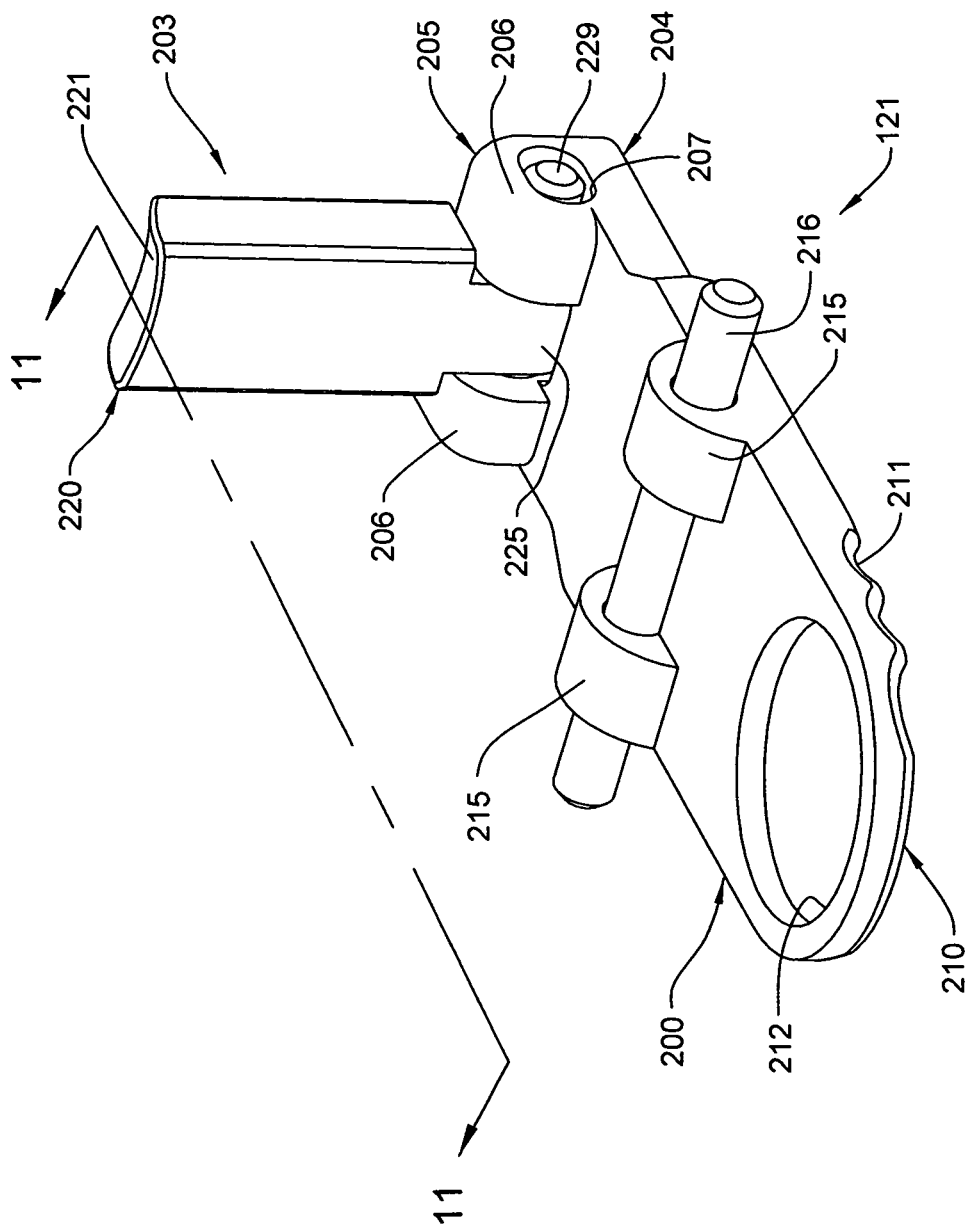
FIG. 9 is an enlarged perspective view of the locking assembly of the coupling arrangement.
Figure 10:
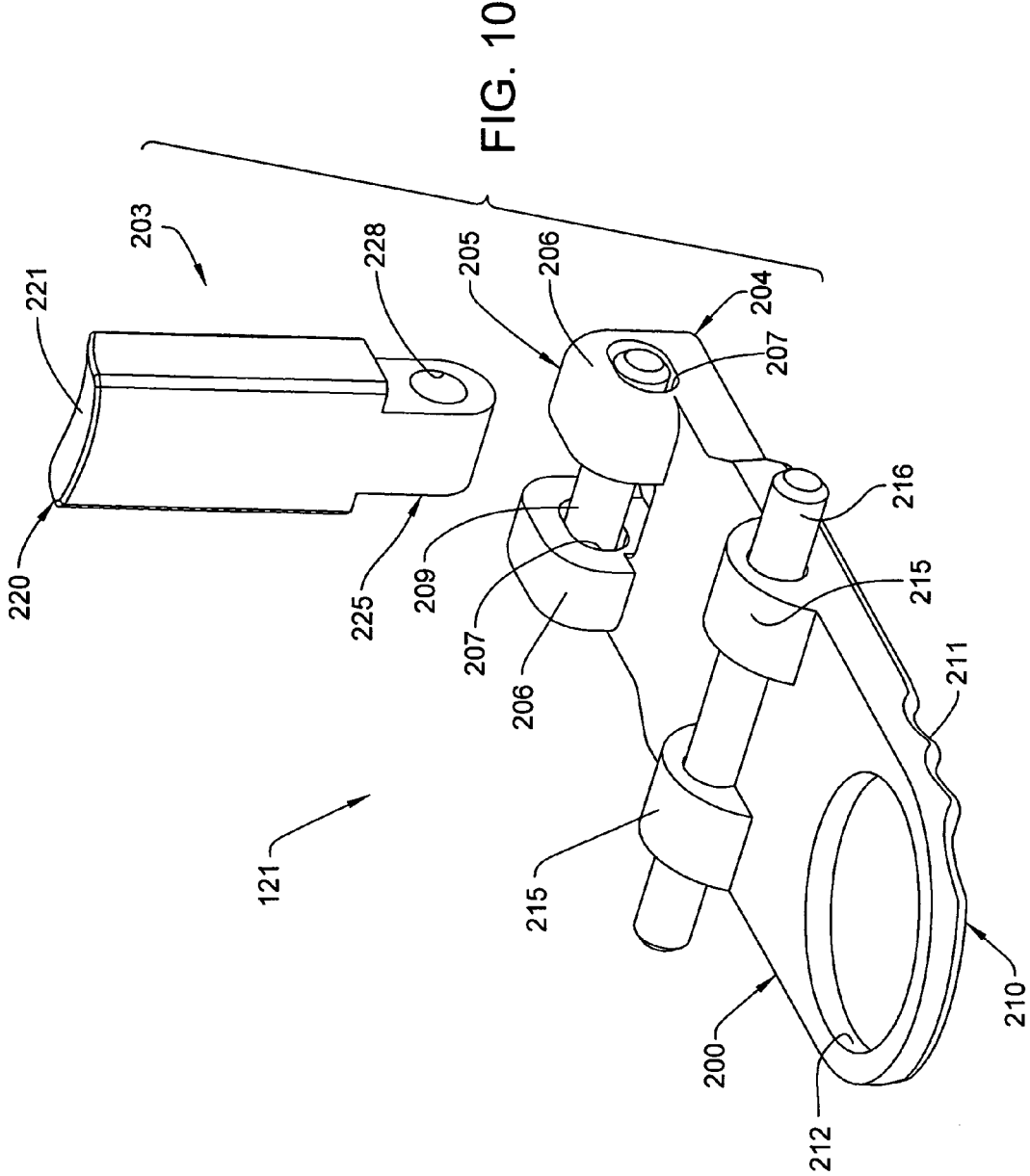
FIG. 10 is an enlarged and partially exploded perspective view of the locking assembly.
Figure 11:
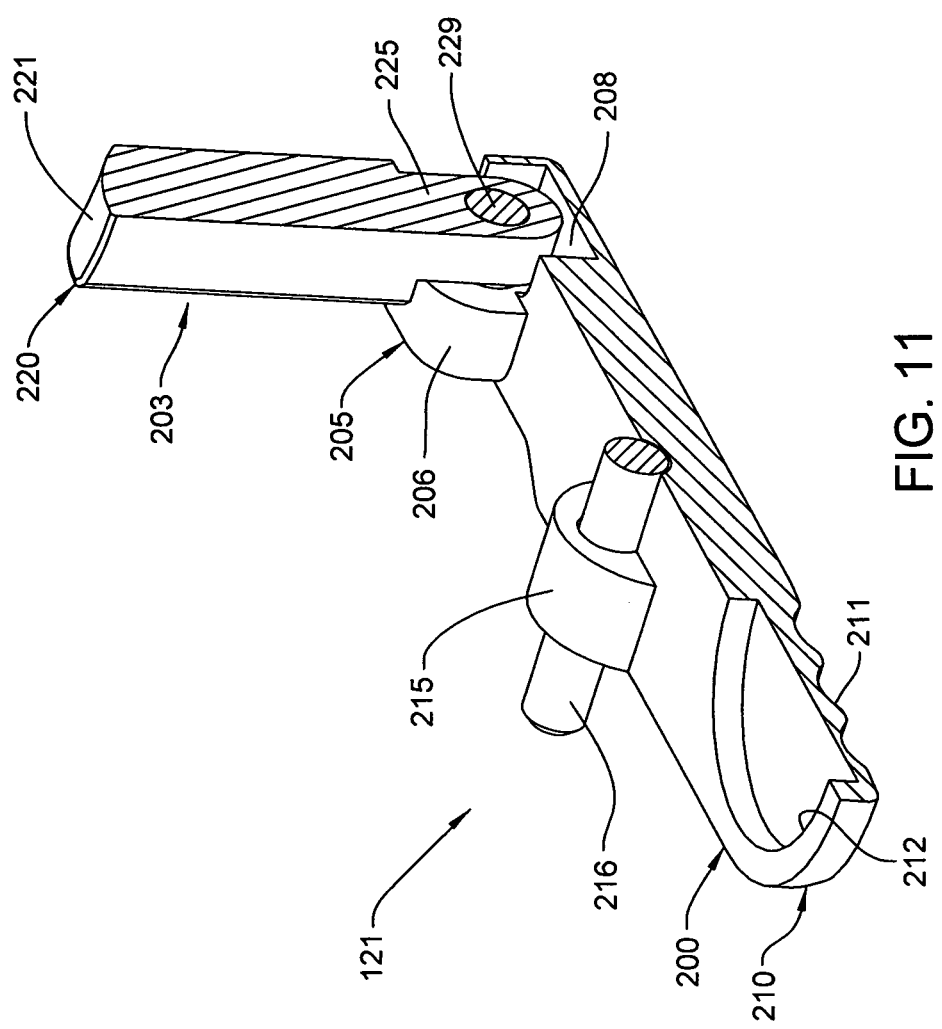
FIG. 11 is an enlarged longitudinal cross-sectional view of the locking assembly, as seen generally along line 11-11 in FIG. 9.

With reference to FIGS. 2, 3 and 8, handpiece housing 18 defines therein an axially-elongated recess 232 along a lower side thereof adjacent collet 53. Recess 232 opens distally so as to communicate with semi-circular opening 101 at the bottom of collet 53. Housing 18 further defines a recess 233 proximally of collet 53. Recess 233 opens downwardly on housing 18 through recess 232. Further, the sides of housing 18 on opposite sides of recess 232 define therein a pair of aligned openings 234, and housing 18 defines a downwardly-opening channel 235 which extends within housing 18 transverse to axis 16 and is aligned with openings 234.

Locking assembly 121 is assembled to housing 18 by positioning spring 201 in recess 212 and positioning assembly 121 within recess 232 of housing 18 so that the upper end of spring 201 is located within housing recess 233. The slider bar 203 is inserted into opening 101 of coupler 53 and upwardly into channel 100 thereof. Pivot pin 216 is inserted into one of the openings 234 of housing 18, through mounting elements 215 of lock lever 200, and into the opposite opening 234 so as to seat within channel 235. When locking assembly 121 is mounted on housing 18, spring 201 bears against a housing wall 260 which defines the upper extent of recess 233 and biases the lock lever 200 in a clockwise direction about pivot pin 216, which effectively urges the ramped-shaped upper surface 221 of slider bar 203 into lower channel 66 of collet 53 and into housing bore 19. Pushing upwardly on the proximal end 210 of lock lever 200 at gripping surface 211 causes lock lever 200 to pivot in a counter-clockwise direction about pin 216, which causes slider bar 203 to translate downwardly or out of channel 100 of collet 53.

Referring to FIGS. 12-26, the combined electrosurgical and mechanical cutting instrument 13 will now be described. Instrument 13 generally includes a hub assembly 300 and a tube assembly 301 connected thereto. Tube assembly 301 includes an outermost tube 303 which in one embodiment is a heat-shrink insulating tube, a tubular housing element 302 and an electrode-supporting barrel 304. Housing element 302 and barrel 304 are disposed in side-by-side relation with one another and surrounded by outermost tube 303. Tube assembly 301 additionally includes a rotatable cutting element 305 disposed within housing element 302, an insulator 307 supported at the distal end of barrel 304 and an electrode 308 supported by insulator 307.

Hub assembly 300 of instrument 13 is fixed to the proximal end of tube assembly 301, and is defined by a generally tubular base body 309. Base body 309 defines therein a pair of generally rectangular and diametrically-opposed openings 310 adjacent a proximal end 311 thereof. Base body 309 also has formed thereon a pair of outwardly-projecting, diametrically opposed and generally ramp-shaped ears 312 disposed distally of openings 310. Ears 312 cooperate with coupling assembly 52 of handpiece 11 to secure instrument 13 therein. Base body 309 has a distal end defined by a head or nose 313 which is generally shaped as a truncated cone and has thereon a plurality of ribs 314 which diverge outwardly as same project in the distal to proximal direction. Ribs 314 terminate distally at a neck 315 which defines the distalmost portion of base body 309. Further, base body 309 defines therein a bore 316 which extends completely through the axial extent base body 309. Bore 316 has a distal counterbore 318 which opens distally through neck 315 and proximal counterbore 320 which opens proximally through end 311 and with which openings 310 of base body 309 communicate. Base body 309, in the illustrated embodiment, is constructed of plastic.

Figure 6:
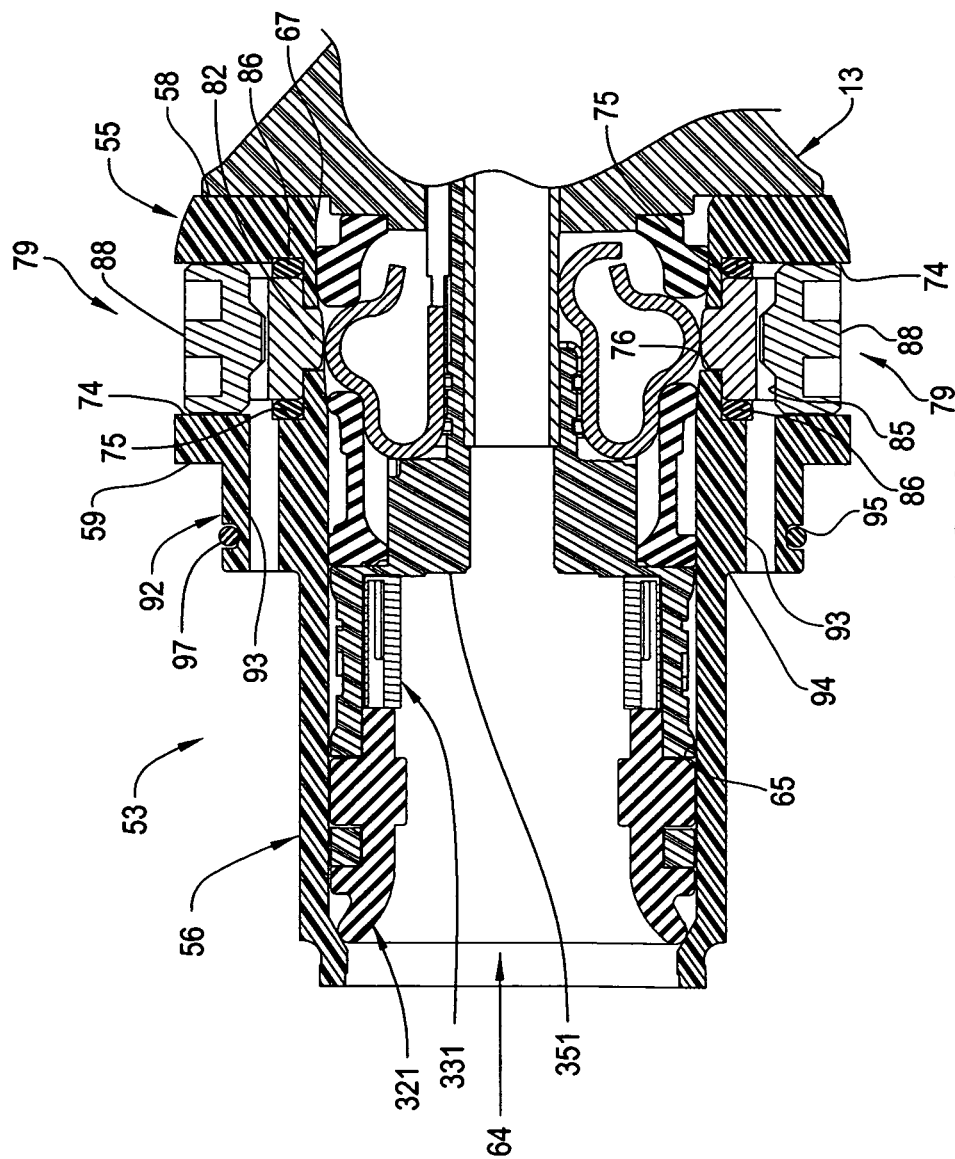
FIG. 6 is an enlarged cross-sectional view of the coupler of FIG. 4, as seen generally along line 6-6 in FIG. 4, and with the tool of FIG. 12 attached.
Figure 14:
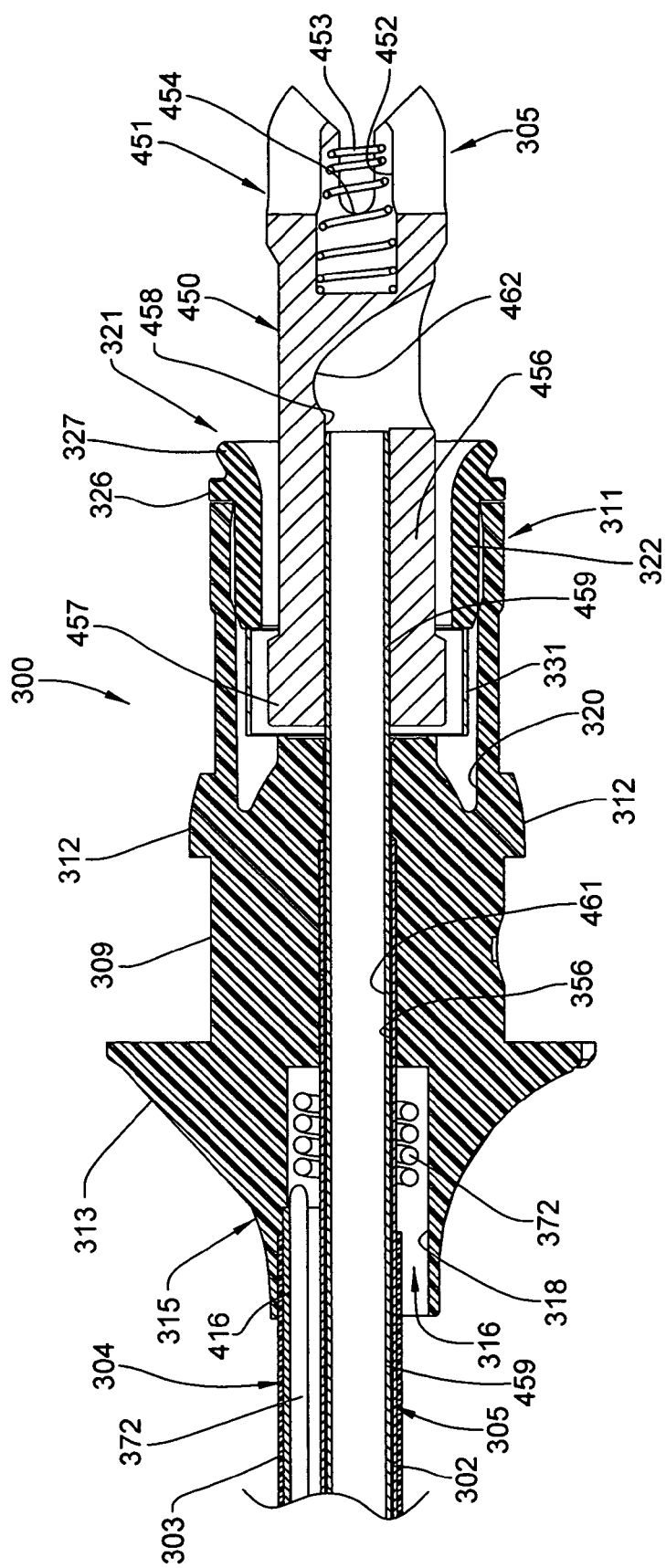
FIG. 14 is an enlarged and fragmentary cross-sectional view of the proximal end of the tool of FIG. 12, as seen generally along line 14-14 in FIG. 13.
Figure 21:
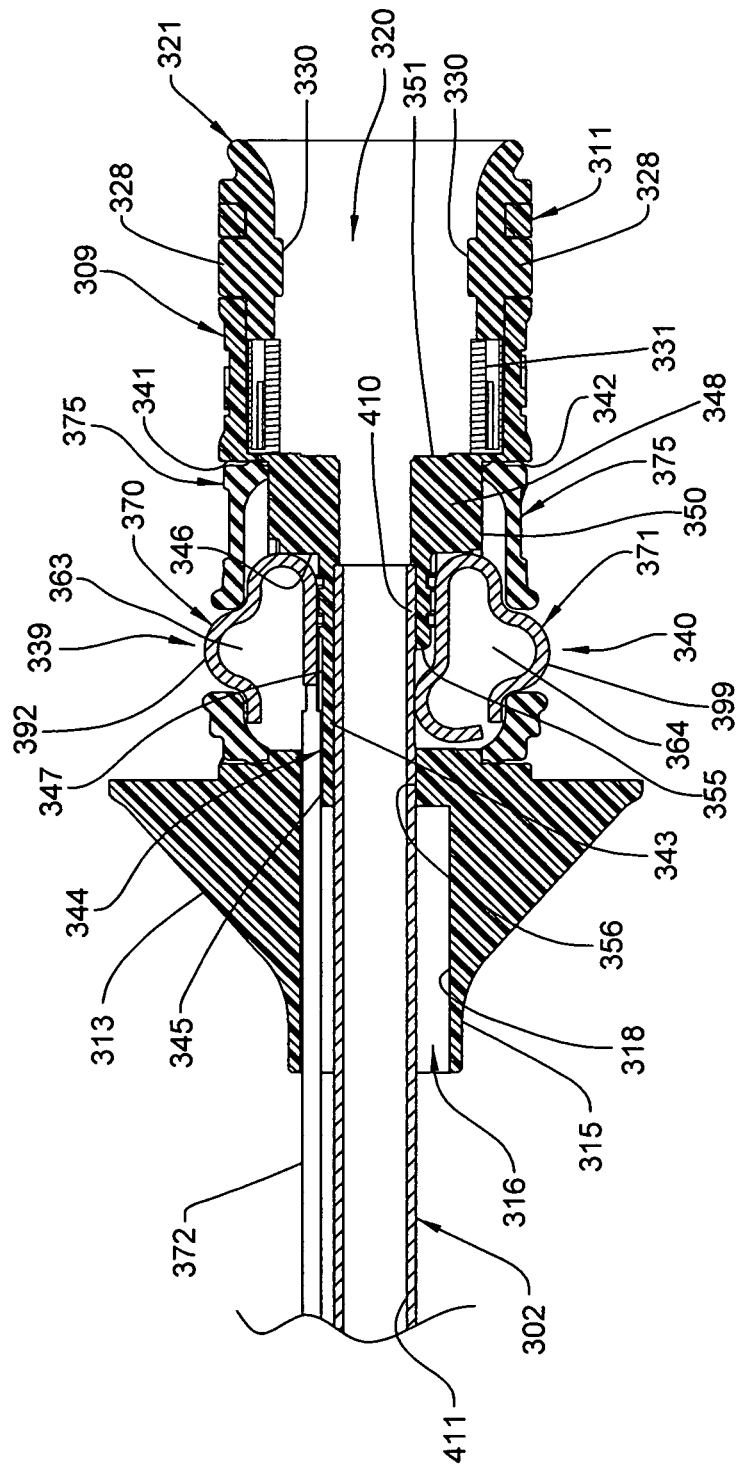
FIG. 21 is an enlarged and fragmentary cross-sectional view of the hub assembly of the tool of FIG. 12, as seen generally along line 21-21 in FIG. 12.

An annular seal 321 is disposed within the open proximal end 311 of base body 309 within counterbore 320. Seal 321 is constructed of a resilient elastomeric material, and is defined by a main section 322 and axially-spaced proximal and distal sections disposed at respective opposite ends of the main section 322. The proximal section defines thereon a pair of annular ribs 326 and 327, which are disposed in sealing engagement with inner annular surface 65 of collet 53 of handpiece 11 when instrument 13 is coupled thereto, as shown in FIGS. 3 and 6. The distal section, as shown in FIG. 21, defines thereon a pair of outwardly projecting and diametrically-opposed lock tabs 328 which engage within the respective openings 310 of base body 309 to secure the seal 321 to base body 309 and fix the axial position of seal 321 relative thereto. The distal section additionally defines thereon a pair of inwardly projecting and diametrically-opposed stop tabs 330, which are generally radially aligned with the respective lock tabs 328. As shown in FIGS. 14 and 21, the RFID 331, which, in the illustrated embodiment, is encapsulated within a ring structure, is seated within proximal counterbore 320 of base body 309 axially adjacent the distal section of seal 321. The encapsulated RFID 331 is disclosed in U.S. Patent Publication No. 2004/0220602A1 published on Nov. 4, 2004, which publication is owned by the same assignee hereof and is hereby incorporated by reference herein.

Hub assembly 300 mounts thereon a pair of electrical contact assemblies 339 and 340 which cooperate with the respective contact arrangements 79 located on collet 53 of handpiece 11. These contact assemblies 339 and 340 are located on the base body 309 axially between the proximal and distal ends 311 and 313 thereof, and are diametrically opposed to one another along the circumference of base body 309.

Base body 309 defines therein a pair of openings 341 and 342 diametrically opposite one another which are configured to receive the respective contact assemblies 339 and 340 therein. Specifically, base body 309 includes an annular support wall 344 which extends axially and terminates distally at the proximal end of counterbore 318 and proximally at the distal end of counterbore 320. A distal end 343 of support wall 344 defines therein a bore 345 adjacent opening 341 (the upper opening 341 in FIG. 21) which extends axially and communicates at its distal end with counterbore 318 and at its proximal end with opening 341. Support wall 344 additionally includes a radially-enlarged proximal end 348 having an annular and distally-facing contact support surface 346. Contact support surface 346 is oriented generally perpendicular to an outer annular surface 347 of the distal end 343 of support wall 344. Proximal end 348 also defines an annular outer surface 350 oriented generally perpendicular to support surface 346, and a proximally-facing annular surface 351 oriented generally perpendicular to outer surface 350 and defining the terminal distal end of counterbore 320 of base body 309. Proximal end 348 at its radially outer extent is connected to tubular proximal end 311 of base body 309. Annular support wall 344, adjacent lower opening 342, defines an opening 355 which communicates with an intermediate portion 356 of bore 316 located axially between counterbores 318 and 320.

Figure 16:
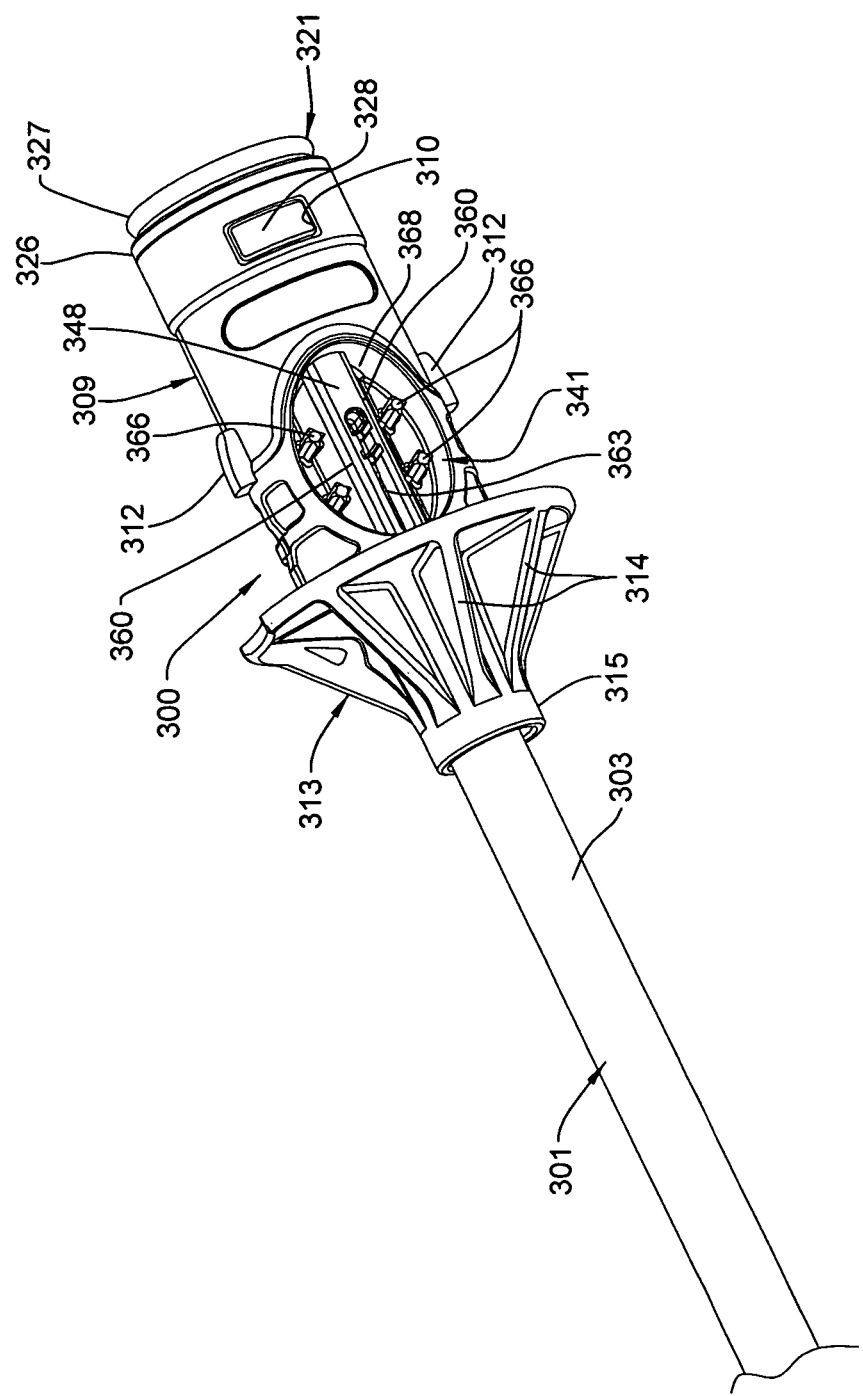
FIG. 16 is an enlarged perspective view of the hub assembly of the tool of FIG. 12, illustrating a mounting recess for the electrical contact assembly.
Figure 17:
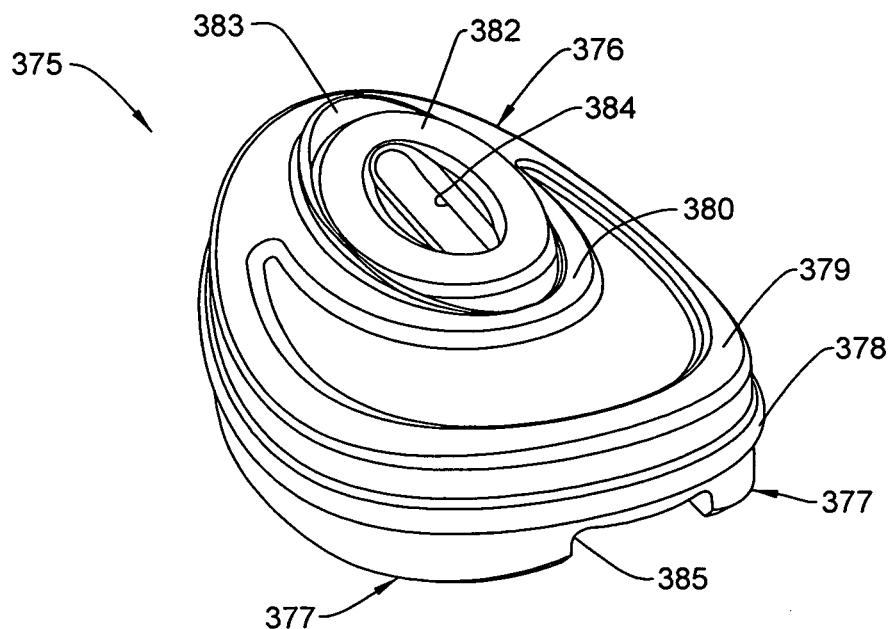
FIG. 17 is an enlarged top perspective view of the seal of the electrical contact assembly of the tool of FIG. 12.

As best shown in FIG. 16, base body 309 has a pair of generally radially-oriented supports or walls 360 located within each of the openings 341 and 342, which supports 360 are joined to and project outwardly from surface 347 of support wall 344, and are joined to and project distally from proximal end 348 of wall 344. Supports 360 are generally parallel to one another and are spaced-apart to define a spring-receiving slot 363, 364 therebetween. Slot 363 located within opening 341 communicates at the radially inner end thereof with bore 345 of support wall 344, and slot 364 at the radially inner end thereof communicates with opening 355 of support wall 344. Further, a pair of post-like mounting projections 366 are fixed to and project outwardly from support wall 344 on opposite sides of each pair of supports 360. As best shown in FIG. 16, each opening 341 and 342 is defined at the outer extent thereof by an annular wall 368 joined to and oriented generally perpendicular to surface 350.

Contact assemblies 339 and 340 each include a spring-like contact 370 and 371 and a sealing member 375. Contact 370 is connected to a lead wire 372 which connects to electrode 308, and contact 371 is electrical contact with housing element 302. Sealing members 375 are identical to one another, and only on of same will accordingly be described herein.

With reference to FIGS. 17-20, sealing member 375 is defined by a top wall 376 and a pair of side walls 377 which project downwardly from respective opposite longitudinal sides of top wall 376. Top wall 376, and sealing member 375 in general, is of a generally elliptical shape. Sealing member 375 includes an annular rib 378 which projects generally sidewardly and defines the outermost perimeter of sealing member 375. Top wall 376 includes a first annular rib 379 which extends around the entire upper periphery of top wall 376 and projects upwardly therefrom, an upwardly-projecting intermediate rib 380 which is arcuate in shape and located inwardly of and adjacent to a proximal portion of first rib 379, and a second upwardly-projecting annular rib 382 located within first rib 379 and surrounded on the proximal side thereof by intermediate rib 380. Top wall 376 additionally includes a distal arcuate rib 383 located in surrounding relation with the distal side of second rib 382. An elongated opening 384 is disposed within and wholly surrounded by second rib 382 and extends completely through top wall 376.

Figure 18:
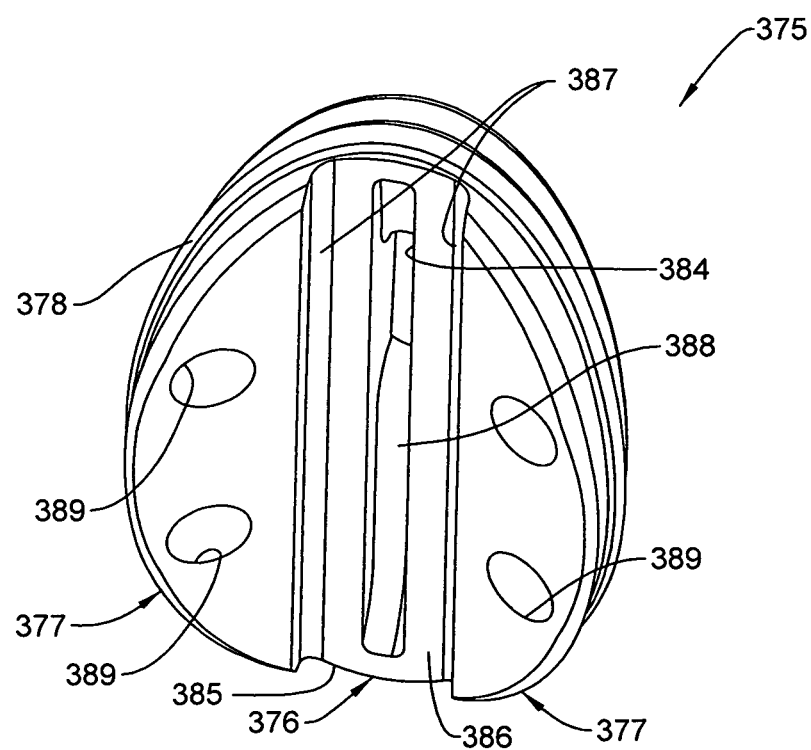
FIG. 18 is an enlarged bottom perspective view of the seal of the electrical contact assembly of the tool of FIG. 12.
Figure 19:
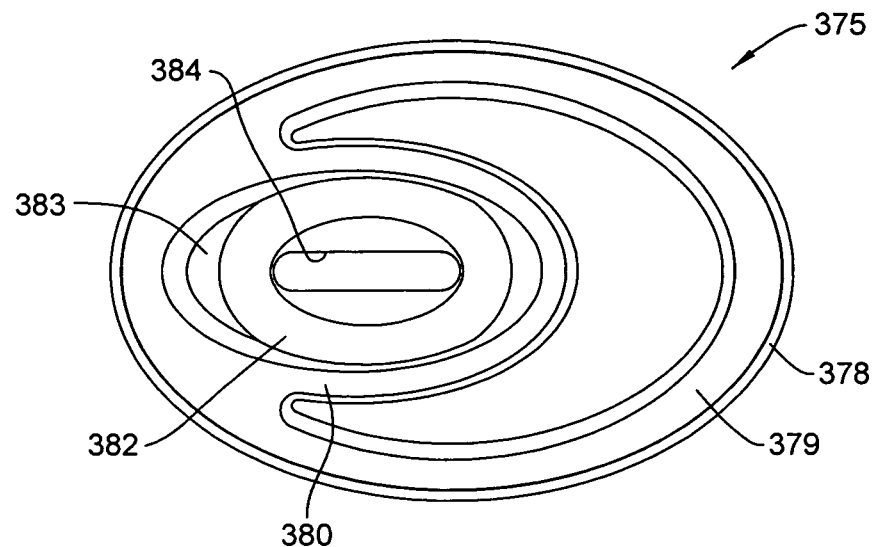
FIG. 19 is an enlarged plan view of the seal of the electrical contact assembly of the tool of FIG. 12.
Figure 20:
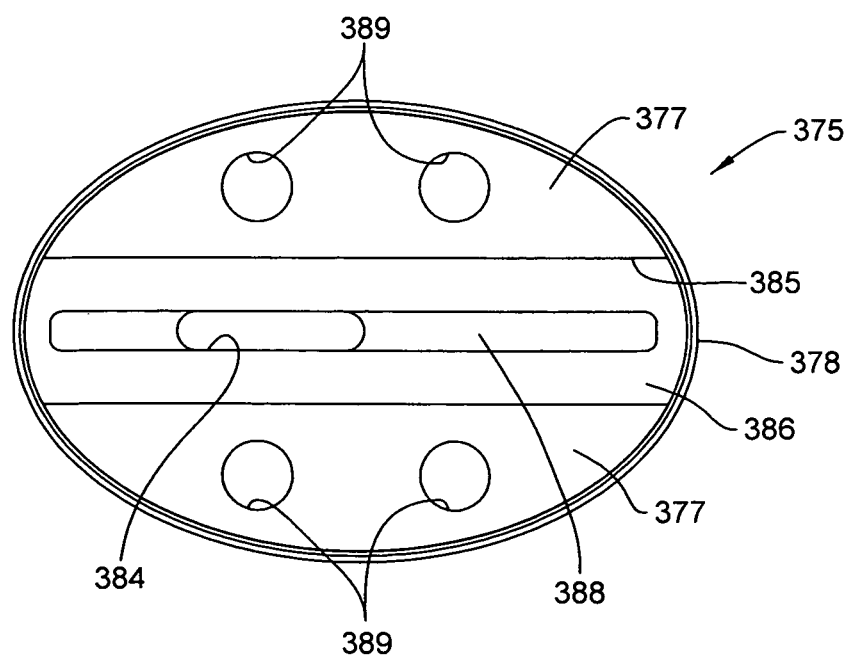
FIG. 20 is an enlarged bottom view of the seal of the electrical contact assembly of the tool of FIG. 12.

Sealing member 375, as best shown in FIG. 18, defines therein an elongated recess 385 which opens downwardly between longitudinal lower edges of side walls 377, and also sidewardly at opposite longitudinal ends of sealing member 375. Recess 385 is defined by an elongated lower surface 386 of top wall 376, and generally parallel and juxtaposed inner surfaces 387 of the respective side walls 377 disposed in generally perpendicular relation with top wall lower surface 386. Lower surface 386 of top wall 376 is generally rectangular in shape, and surrounds a further downwardly-facing surface 388 of top wall 376 which has a longitudinal cross-sectional profile which is contoured so as to generally follow the contour of the upper or outer profile of spring contacts 370 and 371. A pair of downwardly-opening blind holes 389 are axially or longitudinally spaced from one another within each of the side walls 377 so as to open through respective lower surfaces thereof.

Figure 15:
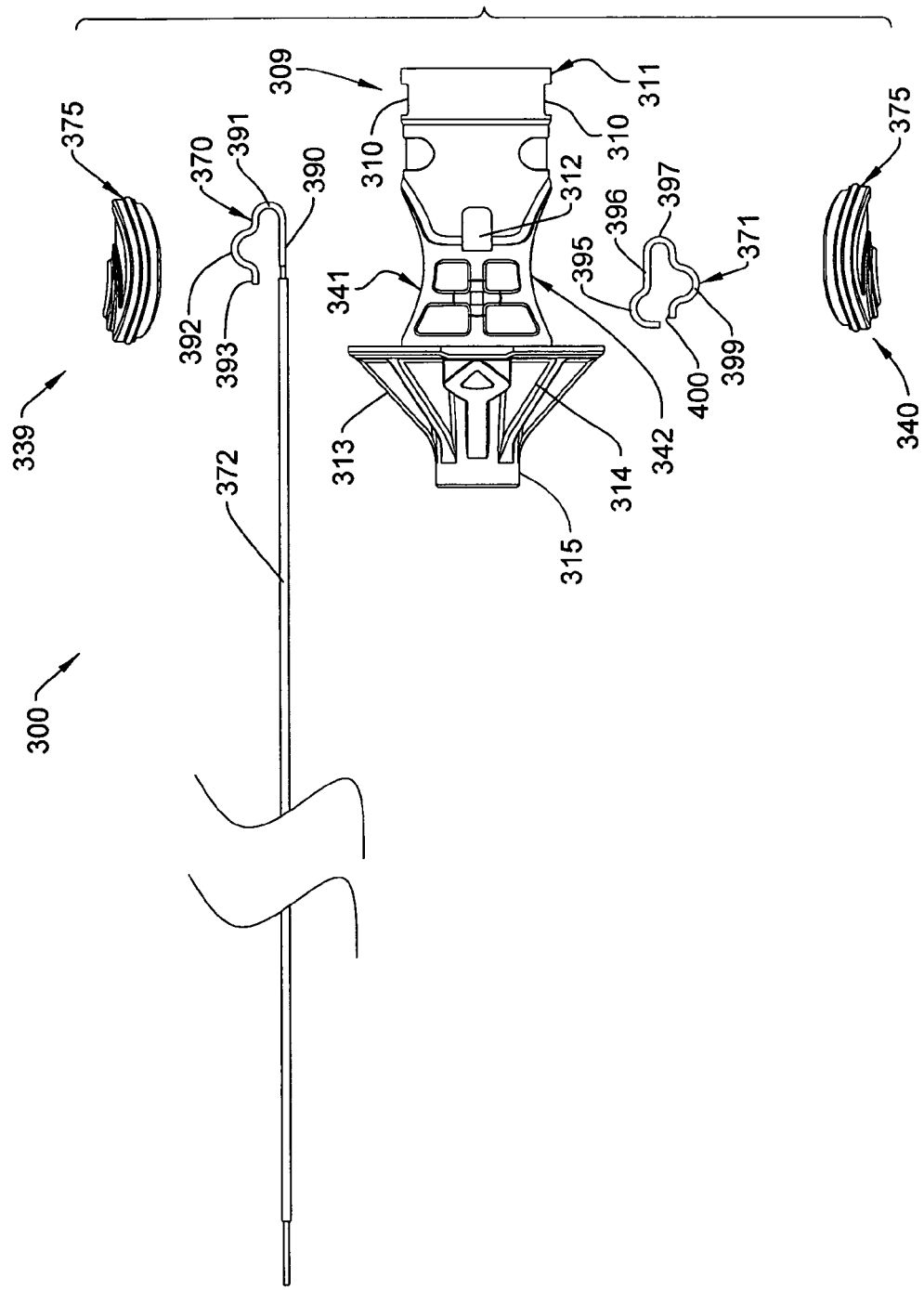
FIG. 15 is an enlarged and fragmentary exploded plan view of the hub assembly of the tool of FIG. 12.

Referring to FIGS. 15 and 21, spring contact 370 of contact assembly 339 includes a straight inner leg 390 having a free distal end connected to lead wire 372, an arcuate proximal leg 391 which extends radially outwardly from the proximal end of inner leg 390, an arcuate outer leg 392 which connects to a distal end of proximal leg 391, and a straight distal leg 393 which is generally parallel to inner leg 390. Spring contact 371 of contact assembly 340 includes an arcuate inner leg 395 which connects at its proximal end to a straight inner leg 396. Straight inner leg 396 connects at its proximal end to a curved proximal leg 397 which extends radially outwardly from inner leg 396 and connects to a curved or arcuate outer leg 399. Outer leg 399 projects radially in the opposite direction from arcuate inner leg 395, and terminates in a straight distal leg 400 which is generally parallel to straight inner leg 396.

Spring contacts 370 and 371 are assembled to base body 309 by inserting each contact 370, 371 into the respective housing recesses 341 and 342. Specifically, spring contact 370 is inserted into slot 363 of housing recess 341 so that inner leg 390 is seated against outer surface 347 of support wall 344, and so that arcuate leg 391 is seated against surface 346 of support wall 344. In this seated position, the free end of inner leg 390 of spring contact 370 is aligned with bore 345 defined in support wall 344, and lead wire 372 can be inserted into counter bore 318 and into bore 345 and electrically connected to the end of inner leg 390 with a crimp. Sealing member 375 is then positioned in housing recess 341 with the second rib 382 oriented distally and so that the legs 377 are located in the respective spaces defined on opposite sides of the support walls 360, and the sealing member 375 is pressed downwardly so that the mounting posts 366 engage upwardly within the correspondingly-located holes 389 on the lower side of sealing member 375. With sealing member 375 mounted within housing recess 341, outer leg 392 of spring contact 370 extends outwardly through opening 384 of sealing member 375, and the free end 393 and outermost portion of proximal leg 391 of spring 370 are disposed adjacent surface 388 of sealing member 375. Further, the lower surfaces of the respective legs 377 of seal 375 are seated against surface 350 of hub support wall 344, recess 385 of seal 375 seats around or over support walls 360, and the rib 378 of seal 375 seats against annular wall 368 of housing 18. It will be appreciated that adhesive or other sealing agent may be applied to mounting posts 366 and/or to appropriate inner surfaces of sealing member 375 to ensure a tight seal between base body 309 and sealing member 375.

Spring contact 371 is inserted into slot 364 of housing recess 342 so that inner leg 395 extends or is seated in opening 355 of support wall 344 so as to project into intermediate portion 356 of bore 316 of base body 309, so that straight inner leg 396 is seated against outer surface 347 of support wall 344, and so that proximal leg 397 is seated against surface 346 of support wall 344. The second sealing member 375 is then positioned in housing recess 342 as described above, that is, so that the second rib 382 is oriented distally and the mounting posts 366 in recess 342 engage in the holes 389 on the lower side of sealing member 375. With sealing member 375 mounted within housing recess 342, outer leg 399 of spring contact 371 extends outwardly through opening 384 of the second sealing member 375, and the free distal leg 400 and the outermost portion of proximal leg 397 are disposed adjacent surface 388 of the second sealing member 375.

Turning now to tube assembly 301 of instrument 13, same is fixed to and projects distally from hub assembly 300. Specifically, housing element 302 has a proximal end 410 fixedly mounted in intermediate portion 356 of bore 316 of base body 309. Housing element 302 itself defines an elongate bore or conduit 411 in which cutting element 305 is disposed. Housing element 302 additionally has a distal end 412 which defines therein a window 413 which communicates with conduit 411, which window 413 opens sidewardly such that the distal end 412 of housing element 302 is generally closed in the axial direction. The edge of housing element 302 which defines window 413 cooperates with cutting element 305 to sever tissue as discussed below. In the illustrated embodiment, the window 413 has a non-toothed configuration. However, it will be appreciated that window 413 may include a toothed configuration or a straight cutting edge depending upon the required type of cutting action. Further, the housing element 302 is constructed of metal, and in the illustrated embodiment is constructed of stainless steel.

As best shown in FIGS. 25 and 26, the electrode-supporting barrel 304 is elongated in shape is defined by an outwardly-arcuate or convex wall 414 which terminates in a pair of longitudinally extending and generally parallel edges 415. The longitudinal edges 415 of the barrel 304 are positioned against the outer surface of housing element 302. Barrel 304 has a proximal end 416 (FIG. 14) fixed within counterbore 318 of hub base body 309 so as to receive lead wire 372, and a distal end 417 defining therein a U-shaped recess 418. In the illustrated embodiment, barrel 304 is constructed of metal, for example, stainless steel.

With reference to FIGS. 23-26, insulator 307 has a main body 420 having an outwardly-arcuate or convex outer surface 421, an inwardly-arcuate or concave inner surface 422 facing away from outer surface 421, and a generally flat end surface 424 which defines the proximal end of insulator 307. The distal end of main body 420 has a U-shaped flange 426 disposed adjacent outer surface 421 and which projects sidewardly outwardly therefrom. Main body 420 defines a bore 430 which extends completely therethrough and opens proximally through end surface 424. Bore 430 defines a pocket 432 at its distal end for receiving electrode 308 therein, which pocket 432 opens both axially and sidewardly through U-shaped flange 426. In the illustrated embodiment, the insulator 307 is constructed of ceramic.

Electrode 308 includes an elongate stem 440 which defines the proximal portion thereof, and an enlarged head 441 fixed to a distal end of stem 440 and which defines the distalmost portion of electrode 308. Head 441, in the illustrated embodiment, includes a plurality, and here six, of tissue-treating projections 443 thereon. It will be appreciated that the configuration of electrode head 441 may vary based upon the type of procedure to be performed. Electrode 308 in the illustrated embodiment is constructed of conductive metal, such as stainless steel or tungsten. However, other suitable materials may be utilized.

Figure 22:
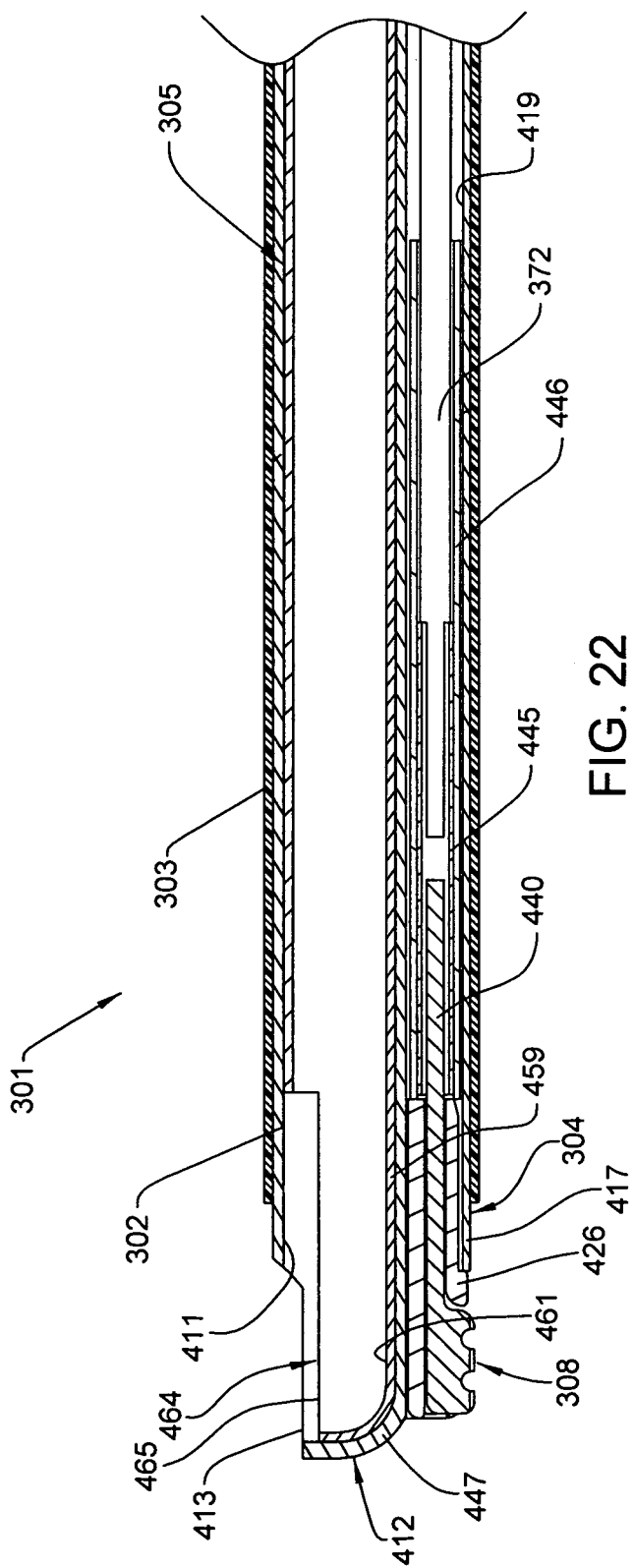
FIG. 22 is an enlarged longitudinal and fragmentary cross-sectional view of the distal end of the tube assembly of the tool of FIG. 12.

Tube assembly 301 is assembled by inserting the stem 440 of electrode 308 into pocket 432 of insulator 307 until electrode head 441 seats within pocket 432 and is surrounded by flange 426 of insulator 307. Adhesive may be used to fixedly secure electrode 308 to insulator 307. With the electrode 308 in this position, the proximal end of stem 440 extends beyond end surface 424, as shown in FIGS. 23 and 24. The proximal end of stem 440 is connected to the distal end of lead wire 372 of hub assembly 300 by a crush tube or crimp 445, and a heat shrink tube 446 is provided over this connection, as shown in FIG. 22.

Electrode 308, insulator 307 and lead wire 372 are positioned along the side of housing element 302 opposite window 413 thereof, and barrel 304 is placed longitudinally along and over the electrode 308, insulator 307 and lead wire 372, so that terminal longitudinal edges 415 are positioned along and in contact with the outer surface of housing element 302 which effectively defines a longitudinally extending channel 419 between wall 414 of barrel 304 and the adjacent outer surface of housing element 302 through which insulator 307, electrode stem 440 and lead wire 372 extend. Further, the proximal end of insulator 307 is positioned within the open distal end 417 of barrel 304, with U-shaped flange 426 of insulator 307 seated within U-shaped recess 418 of barrel 304. Adhesive may be used to securely fasten insulator 307 within the distal end 417 of barrel 304.

Outermost tube 303 is heat-shrunk over barrel 304 and housing element 302 to secure same to one another and to insulate the tube assembly 301 along the majority of the longitudinal extent thereof. In this regard, as shown in FIG. 22, tube 303 terminates just proximally of window 413, which leaves a portion 447 of housing element 302 exposed at the distal end of instrument 13 adjacent electrode 308. Instrument 13 in the illustrated embodiment is configured as a bipolar electrode, wherein head 441 of electrode 308 defines the active, energy-delivering electrode, and portion 447 of housing element 302 defines the return electrode.

The tube assembly 301 is assembled to hub assembly 300 by inserting the proximal end of assembly 301 into counterbore 318. In this regard, the proximal end of housing element 302 is seated within intermediate portion 356 of bore 316 of base body 309 and may be fixed thereto with adhesive. Once housing element 302 is seated within bore portion 356, inner leg 395 of contact 371 is disposed in electrical contact with the outer surface of housing element 302, as shown in FIG. 21. As shown in FIG. 14, the proximal end 416 of barrel 304 and the proximal end of outermost tube 303 seat within counterbore 318 and may be secured thereto with adhesive, and any excess length of lead wire 372 may be stored within proximal end of counterbore 318.

With tube assembly 301 assembled to hub assembly 300 as discussed above, contact 370 is electrically connected to electrode 308 via lead wire 372, and contact 371 is in electrical connection with housing element 302 and thus return electrode 447 defined at the distal end of housing element 302.

Figure 12:
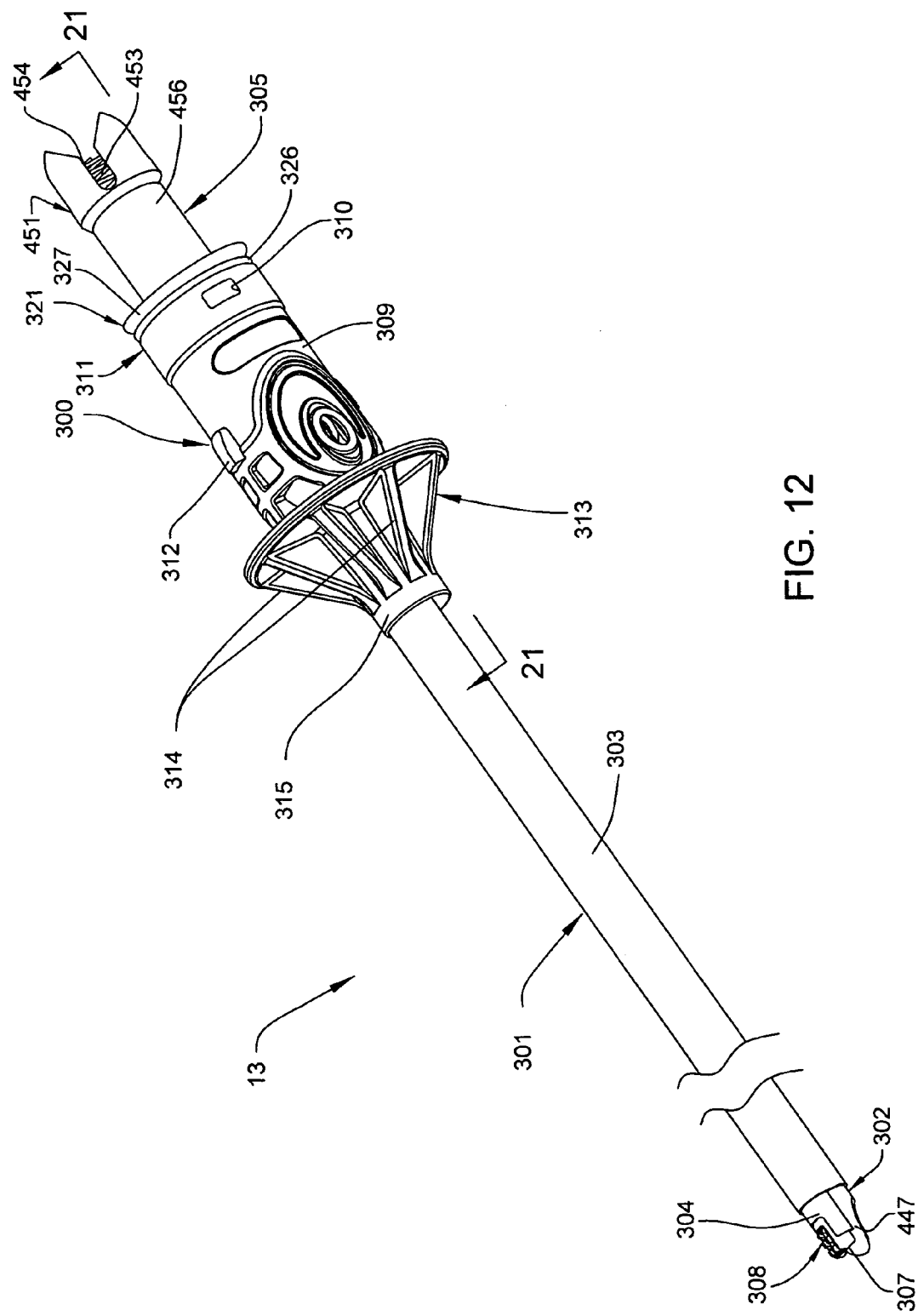
FIG. 12 is a perspective and fragmentary view of a combined electrosurgical and mechanical cutting tool or instrument.
Figure 13:
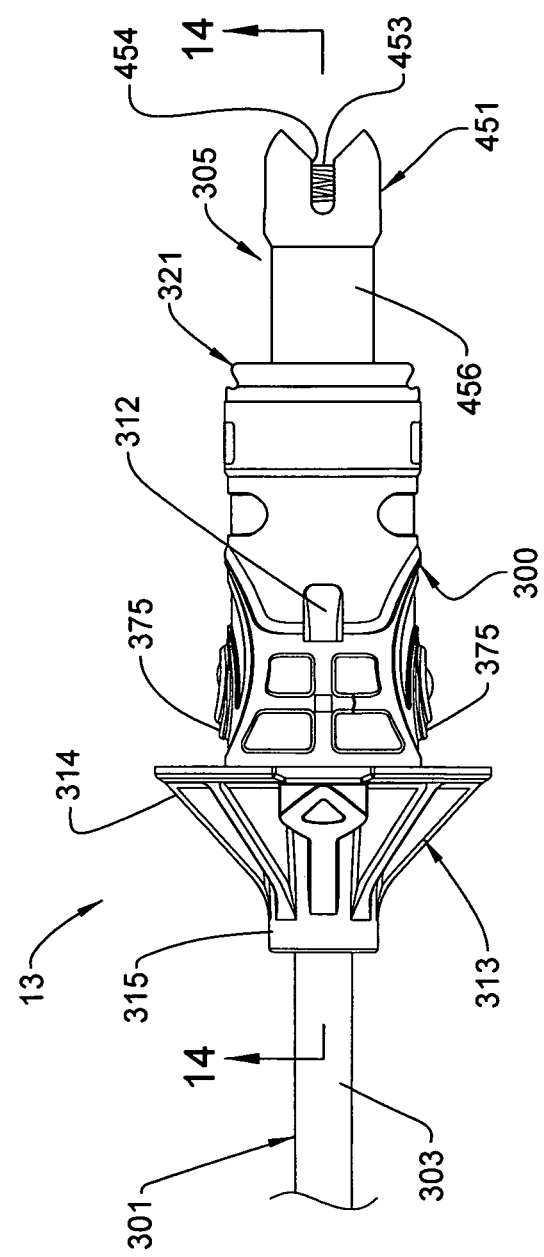
FIG. 13 is an enlarged and fragmentary plan view of the tool of FIG. 12.

Cutting element 305 is of a conventional construction, and will accordingly be only briefly described herein with reference to FIGS. 12, 14 and 22. Cutting element 305 includes a hub 450 which defines the proximal end thereof. Hub 450 includes a motor-engaging drive hub 451 defining a proximally opening bore 452 therein in which a coil spring 453 is located, and a slot 454 which extends transversely to the longitudinal axis of the cutting element 305. Hub 450 additionally includes a neck 456 which extends distally from drive hub 451. Neck 456 terminates at a head 457 which has an enlarged outer diameter as compared to the remainder of neck 456. In this regard, the outer diameter of head 457 is slightly larger than the inward projection of the respective stop tabs 330 of seal 321 (FIG. 21). A bore 458 extends through neck 456 and head 457, in which an elongate and tubular drive shaft 459 is fixed. Drive shaft 459 defines therein a suction passage 461 which is in communication with a suction port 462 defined in neck 456, which suction port 462 is in turn in communication with suction passage 31 of handpiece 11.

Drive shaft 459 includes a cutting element or head 464 at its distal end thereof. Cutting head 464 defines therein a window or opening 465 which communicates with suction passage 461. In the illustrated embodiment, the cutting head 464 includes a straight edge which defines window 465 for severing tissue. However, it will be appreciated that drive shaft 459 may include other types of cutting heads, such as those with toothed cutting edges, a burr, etc. In the illustrated embodiment, drive shaft 459 is constructed of metal, for example stainless steel.

The cutting element 305 is assembled to hub assembly 300 by inserting the distal end of drive shaft 459 into counterbore 320 at the proximal end 311 of base body 309. During this insertion, the enlarged head 457 of hub 450 compresses the seal 321 and head 457 pushes past the stop tabs 330, at which point the seal 321 resumes its original shape. The stop tabs 330, while allowing some axial displacement of cutting element 305 relative to hub assembly 300, prevent the cutting element 305 from detaching or falling out of the hub assembly 300 due to gravitational forces.

The assembled instrument 13 is secured to the handpiece 11 as follows, and with reference to FIG. 3. Instrument 13 is attached to the handpiece 11 by inserting the hub 450 of cutting element 305 and hub assembly 300 into the open distal end 55 of collet 53 by aligning ears 312 of base body 309 with the respective channels 66 of collet 53. As instrument 13 is inserted into collet 53, the ear 312 adjacent the lower side of handpiece 11 engages the rounded uppermost surface 221 of slider bar 203 of locking assembly 121, causing movement of slider bar 203 outwardly, which in turn causes pivoting movement of lock lever 200 about pivot pin 216 in a counterclockwise direction. This pivoting movement of lock lever 200 effectively compresses spring 201 inwardly against handpiece housing 18. Once the ear 312 is moved proximally past surface 221 of slider bar 203, the spring 201 urges the lock lever 200 in the clockwise direction and causes the upper end 220 of slider bar 203 to move inwardly again into channel 66 of collet 53. In this locked position of locking assembly 121, the upper end 220 of slider bar 203 is positioned just distally of the distal surface of ear 312, and will prevent dislodgement or removal of tool 13 from handpiece 11. To release instrument 13 from handpiece 11, the user presses inwardly on the lock lever 200 at gripping surface 211, which compresses spring 201 and causes movement of slider bar 203 in the outward direction so that the ear 312 can be moved in the distal direction past the upper end 220 of slider bar 203 which allows removal of the instrument 13 from handpiece 11.

If for some reason the instrument 13 is pulled in the distal direction away from handpiece 11 when the locking assembly 121 is in the locked position, the pivoting connection between slider bar 203 and lock lever 200 and the elongated openings 207 defined in mounting elements 206 allow for some play between the slider bar 203 and lock lever 200, which will effectively prevent unintended release of the locking assembly 121.

The above securement of the tool 13 to handpiece 11 causes the drive hub 451 of cutting element 305 to engage the motor output shaft 23. More specifically, the pin 24 of shaft 23 seats within slot 454 of drive hub 451, such that the rotational movement of the shaft 23 is transferred to the cutting element 305. The spring 453 of drive hub 451 biases the cutting element 305 forwardly or in the distal direction, so as to maintain the cutting head 464 of cutting element 305 in bearing contact with the interior of the closed distal end 412 of the static housing element 302.

Additionally, the securement of instrument 13 to handpiece 11 places contacts 370 and 371 in electrical contact with the respective contacts 80 of collet 53, which provides electrical power to electrode 308 and allows housing element 302 to function as a return via its return electrode 447. As shown in FIG. 6 which illustrates in cross-section the instrument 13 inserted within collet 53 without cutting element 305, the insertion of hub assembly 300 of tool 13 into collet 53 causes inward compression of the outermost legs of the respective spring contacts 370 and 371 towards the respective inner legs of contacts 370, 371, which provides each of the spring contacts 370 and 371 with an outwardly-directed bias so that the outer arcuate legs 392 and 399 maintain contact with the corresponding contacts 80 of handpiece 11. Further, the inner surface 65 of collet 53 causes compression of seals 375 axially against surface 368 of hub base body 309 and around outer arcuate legs 392 and 399 of contact members 370 and 371, and radially against surface 65 of collet 53. More specifically, ribs 382 and 383 sealingly engage surface 65 of collet 53, and rib 378 engages surface 368 of base body 309.

While cutting element 305 is described herein as including a drive shaft 459 and cutting head 464 which are rotatable relative to housing element 302, it will be appreciated that cutting element 305 may alternatively include a component which moves axially or translationally relative to housing element 302.

In operation, handpiece 11 is connected to control unit (CU), and tool 13 is inserted into handpiece 11 as described above. In this regard, the RFID 331 provided in tool 13, which is read by the coil 112 of handpiece 11, contains information which identifies the tool 13 to the control unit (CU), tool operating parameters, default settings, operation restrictions, etc. The distal end of tool 13 is inserted into the surgical site, and can be utilized to perform multiple functions simultaneously or separately from one another. If desirable or necessary, the distal end of tool 13 can be inserted into the surgical site through a working portal defined by a conventional cannula or trocar (not shown). The tool 13 is operable as a cutter for mechanically cutting tissue via cutting element 305 and as an electrosurgical tool for the purpose of cauterizing or ablating tissue utilizing electrode 308. In this regard, control unit (CU) supplies electrical power to the motor 20 of handpiece 11 in order to actuate cutting element 305, and also includes an electrosurgical generator. The generator is capable of generating two types of radio-frequency electrosurgical waveforms or signals, namely, a low-power signal which enables electrode 308 to coagulate fluid, such as blood, to seal tissue at the surgical site, and a high-power signal which enables electrode element 308 to vaporize tissue or remove same.

The buttons 134 provided on handpiece 11 are utilized to select the mode of operation of cutting element 305 to control motor 20 so as to drive cutting element 305 in a forward or reverse direction, or in an oscillating manner. Actuation of cutting element 305 causes same to rotate within and relative to outer housing element 302. In this regard, the cutting head 464 of cutting element 305 is rotated past the cutting edge of static housing element 302 which defines window 413, which serves to cut tissue located adjacent or within cutting window 413. Buttons 134 are also utilized to select the coagulation mode or the ablation mode for electrode 308. Selection of the coagulation mode causes the control unit (CU) to send the appropriate signal to electrode 308 via the contact 80 of collet 53 associated with spring contact 370, so as to apply electrical current to the targeted tissue via electrode 308. The surgeon can also select the ablation mode if tissue removal (or "cutting") is desired by depressing the appropriate button 134, and control the cut level by depressing the appropriate button 134.

The functionality of the various buttons 134 provided on handpiece 11 is based on the particular user's preferences. Specifically, a surgeon's preferences for operation of tool 13 are created and stored in a file which is loaded into control unit (CU) prior to a surgical procedure, wherein the buttons 134 are mapped by the control unit (CU) to carry out particular operational controls as desired by the surgeon. In this regard, buttons 134 can be provided with different colors, such as gray, blue and yellow, to allow the surgeon to easily locate the proper button 134. The surgeon may want to have each button 134 carry out a single function of either cutting element 305 or electrode 308, or alternatively have selected buttons carry out multiple functions. For example, the surgeon may want to have one button 134 actuate mechanical cutting (using cutting element 305) in a forward mode, another button to cause coagulation (using electrode 308), and the third button to actuate the oscillating mode of the cutting element 305. Alternatively, the surgeon may want to have one button 134 actuate a simultaneous mechanical cutting mode (using cutting element 305) and ablation mode (using electrode 308). In this case, one button 134 is mapped by the control unit (CU) so that when this button 134 is depressed, cutting element 305 and electrode 308 are actuated simultaneously. The above modes of operation are provided as examples only, and the mapping of buttons 134 may be carried out in various modes and combinations of functions based on the user's preference and/or the surgical procedure to be carried out.

It will be appreciated that when desirable or necessary, cut tissue and other surgical debris or fluids can be removed by suction through windows 413, 465 and suction passage 461 of drive shaft 459, through suction port 462 and suction passage 31 and suction bore 30 of handpiece 11, and ultimately through the suction tube (not shown) connected to fitting 32. Such suction is controlled via valve 34.

Alternatively, the control unit (CU) may be associated with a switch, either through a suitable cable or wirelessly, to allow the surgeon to operate the controls or the handpiece 11 remotely. Such a switch may be a footswitch or a hand switch.

It will be appreciated that the control functions of the handpiece 11 as discussed above which are carried out through buttons 134 may alternatively be performed directly at the control unit (CU), which control unit (CU) would then include appropriate control buttons so as to allow the user to select the desired operations of handpiece 11.

Figure 27:
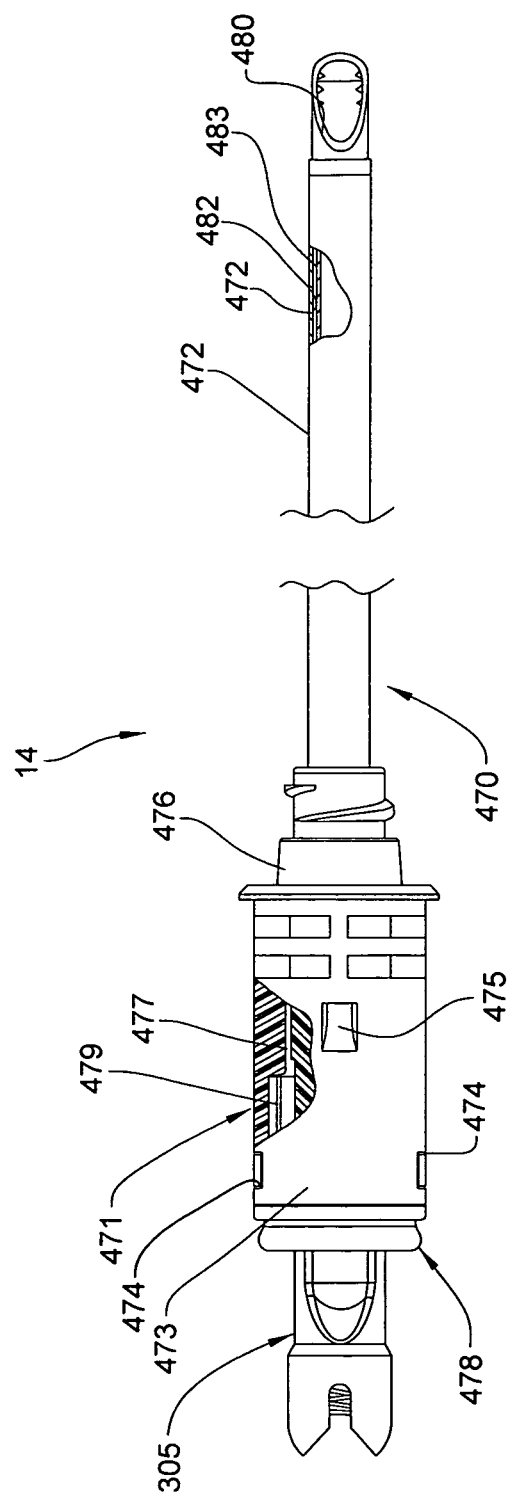
FIG. 27 is a fragmentary and partial cross-sectional plan view of a cutter or shaver tool.

Turning now to surgical shaver or cutter instrument 14, same is illustrated in FIG. 27. Instrument 14 is conventional, and is sold by the assignee hereof under Part No. 475-000-200. Instrument 14 will accordingly be only briefly described here. Instrument 14 includes an outer housing assembly 470 having a hub 471 and an elongated outer tube 472 projecting outwardly from and connected to the hub 471. Hub 471 has a generally tubular base body 473, which defines therein a pair of generally rectangular and diametrically opposed openings 474 adjacent the proximal end thereof similar to openings 310 of hub assembly 300 of tool 13. Base body 473 also has formed thereon a pair of outwardly projecting, diametrically opposed and generally ramped-shaped ears 475 disposed distally of openings 474 and rotationally offset 90 degrees therefrom. Hub 471 has a distal end defined by a head or nose 476 of a reduced diameter as compared to base body 473. Further, hub 471 defines therein a bore 477 which extends completely through the hub 471, and with which openings 474 of base body 473 communicate. An annular seal 478 is disposed within the proximal end of bore 477 of hub 471. Seal 478 is essentially identical to seal 321 of hub assembly 300 of instrument 13, and will not be described further here. Hub 471 additionally includes an RFID 479 (similar to RFID 331) encapsulated within a ring structure and seated within hub bore 477 of hub 471 axially adjacent the distal portion of seal 478.

Outer tube 472 of instrument 14 defines a cutting window 480 and an interior conduit 482 in which a cutting element is disposed. This cutting element is essentially identical to cutting element 305 described above relative to instrument 13, and thus is provided with the same reference number and will accordingly not be described here.

Shaver instrument or tool 14 is mounted to handpiece 11 in a similar manner as described above relative to instrument 13. Briefly, hub 471 is inserted into the open distal end 55 of collet 53 by aligning ears 475 of hub 471 with the respective collet channels 66. As instrument 14 is advanced into collet 53, one of the ears 475 engages the slider bar 203 of locking assembly 121, causing pivoting movement of lock lever 200 in a counterclockwise direction. Once the ear 475 is moved proximally past surface 221 of slider bar 203, the lock lever 200 rotates and causes the upper end 220 of slider bar 203 to move inwardly again into channel 66 of collet 53 to prevent removal of tool 14 from handpiece 11. Release of instrument 14 from handpiece 11 is effected by pressing inwardly on the lock lever 200 and pulling the instrument 14 in the distal direction out of the handpiece 11.

With the instrument 14 installed in handpiece 11 as described above, output shaft of 23 of motor 20 drivingly engages the cutting element 305 and rotates same relative to outer tube 472 to sever patient tissue. Suction can also be drawn through cutting element 305 in order to remove fluid and other surgical debris from the surgical site. When utilizing this type of surgical instrument, the electrical contact arrangements 79 of collet 53 of the handpiece 11 are not utilized, since this type of instrument does not require electrical power to power any on-board component.

The tool 14 is controlled by control unit (CU), which control unit (CU) supplies electrical power to the motor 20 of handpiece 11 in order to actuate cutting element 305. The buttons or switches 134 on handpiece 11 are utilized to control the mode of operation of cutting element 305, to control motor 20 so as to drive cutting element 305 in a forward or reverse direction, or in an oscillating manner, as is conventional. When mechanical cutting of tissue is desired, then motor 20 is activated by the appropriate buttons 134 on handpiece 11 so as to cause cutting element 305 to rotate within and relative to outer tube 472. The cutting head of cutting element 305 is rotated past the cutting edge of static outer tube 472 which defines window 480, which effectively cuts tissue located adjacent or within cutting window 480.

Electrosurgical instrument or probe 15 will now be described with reference to FIGS. 28-31. Instrument 15 has a hub assembly 500 which is similar to hub assembly 300 of instrument 13, and components of hub assembly 500 which are similar or identical to components of hub assembly 300 will utilize the same reference number, plus two-hundred. A detailed description of all components of hub assembly 500 will accordingly not be provided, since reference can be made to the above description of hub assembly 300 for an understanding of hub assembly 500. Instrument 15 additionally includes a tube assembly 600 projecting distally from the hub assembly 500.

Hub assembly 500 of instrument 15 is fixed to the proximal end of tube assembly 600, and is defined by a generally tubular base body 509. Base body 509 defines therein a pair of generally rectangular and diametrically-opposed openings 510 adjacent a proximal end 511 thereof. Base body 509 also has formed thereon a pair of outwardly-projecting, diametrically opposed and generally ramp-shaped ears 512 disposed distally of openings 510, which ears 512 cooperate with collet 53 of handpiece 11 to secure instrument 15 therein. Base body 509 has a distal end defined by a head or nose 513 having thereon a plurality of ribs 514 which terminate distally at a neck 515. Further, base body 509 defines therein a bore 516 which extends completely through base body 509. Bore 516 has a proximal counterbore 520 which opens proximally through end 511 and with which openings 510 of base body 509 communicate. Base body 509, in the illustrated embodiment, is constructed of plastic.

Figure 30:
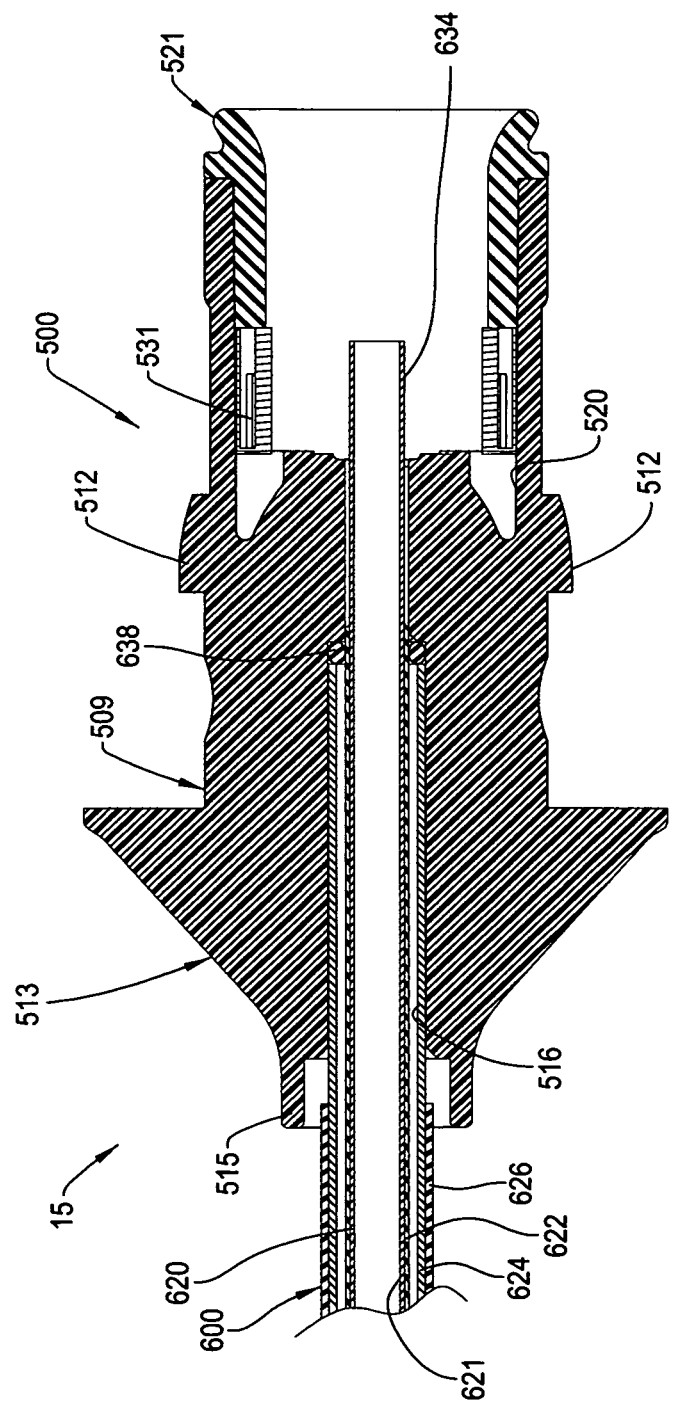
FIG. 30 is an enlarged and fragmentary view of the proximal end of the electrosurgical instrument of FIG. 28, as seen generally along line 30-30 in FIG. 29.
Figure 31:
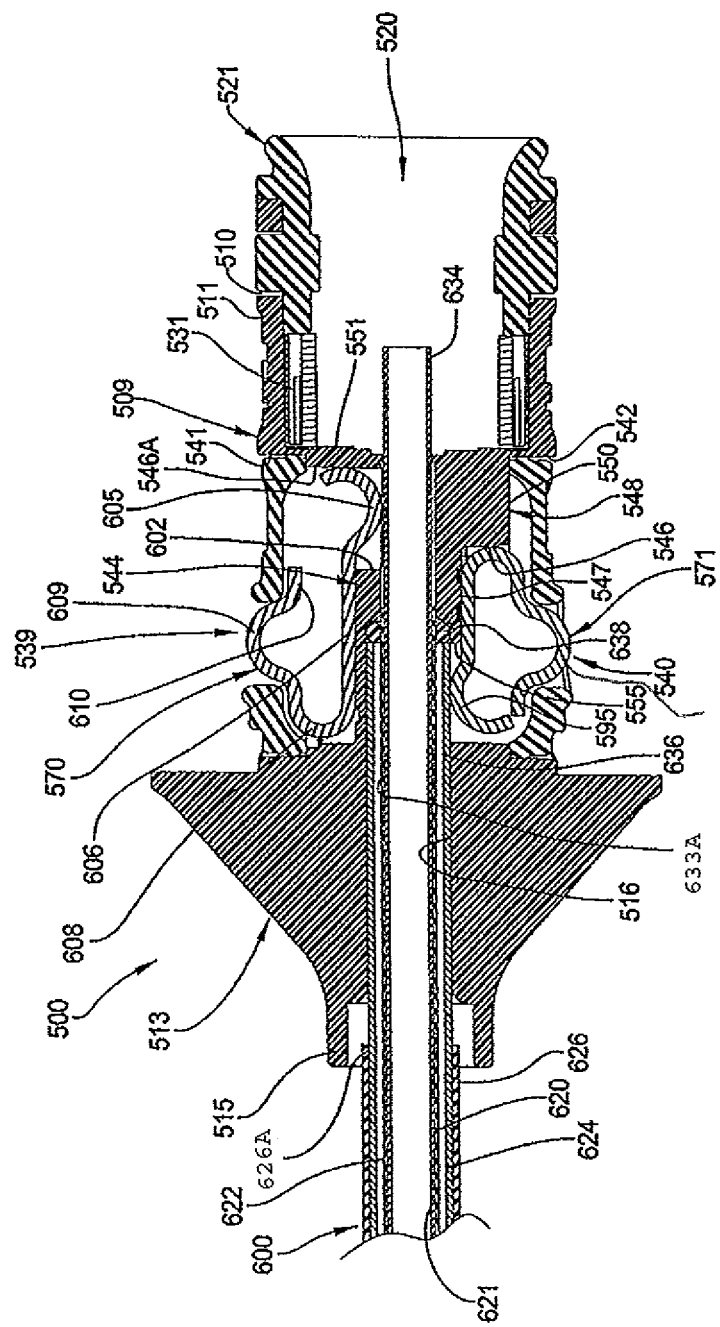
FIG. 31 is an enlarged and fragmentary view of the proximal end of the electrosurgical instrument, as seen generally along line 31-31 in FIG. 28.

A seal 521 is disposed within the proximal counterbore 520 of base body 509. As shown in FIGS. 30 and 31, a RFID 531 is seated within proximal counterbore 520 of base body 509 axially adjacent the distal section of seal 521.

Hub assembly 500 mounts thereon a pair of electrical contact assemblies 539 and 540 which cooperate with the respective contact arrangements 79 located on collet 53 of handpiece 11. Contact assemblies 539 and 540 are located on the base body 509 axially between the proximal and distal ends 511 and 513 thereof, and are diametrically opposed to one another along the circumference of base body 509.

Base body 509 defines thereon a pair of openings 541 and 542 diametrically opposite to one another and configured to receive the respective contact assemblies 539 and 540 therein. Specifically, base body 509 includes an inner support wall 544 adjacent openings 541 and 542 which extends proximally from nose 513 and terminates distally at the distal end of counterbore 520. Support wall 544 additionally includes a proximal end 548 which, adjacent contact assembly 540, has an annular and distally-facing contact support surface 546, and a distally-facing contact support surface 546A adjacent contact assembly 541. Support surface 546A is located closer to proximal end 511 of base body 509 than surface 546. Contact support surfaces 546 and 546A are oriented generally perpendicular to an outer annular surface 547 of support wall 544. Proximal end 548 also defines an annular outer surface 550 oriented generally perpendicular to support surfaces 546 and 546A, and a distally-facing annular surface 551 oriented generally perpendicular to outer surface 550 and defining the terminal distal end of counterbore 520 of base body 509. Annular support wall 544, adjacent lower opening 542, defines an opening 555 which communicates with bore 516, and adjacent upper opening 541 defines an opening 602 therein which communicates with bore 516. Openings 555 and 602 are axially offset from one another, with opening 555 being located distally of opening 602. Proximal end 548 at its radially outer extent is connected to proximal end 511 of base body 509.

Similar to supports 360 of base body 309 of instrument 13, base body 509 has a pair of generally radially-oriented supports located within each of the openings 541 and 542, which supports are generally parallel to one another and are spaced-apart to define a spring-receiving slot therebetween. The slot located within opening 541 communicates at the radially inner end thereof with opening 602 of support wall 544, and the slot located within opening 542 at the radially inner end thereof communicates with opening 555 of support wall 544.

Contact assemblies 539 and 540 each include a spring-like contact 570 and 571 and a sealing member 575. Sealing members 575 are identical to sealing members 375 and will accordingly not be described here. Referring to FIG. 31, spring contact 570 of contact assembly 539 includes an arcuate inner leg 605 which connects at its distal end to a straight inner leg 606. Straight inner leg 606 connects at its distal end to a curved distal leg 608 which extends radially outwardly from inner leg 606 and connects to a curved or arcuate outer leg 609. Outer leg 609 projects radially in the opposite direction from arcuate inner leg 605, and terminates in a straight distal leg 610 which is generally parallel to straight inner leg 606. Spring contact 571 is identical to spring contact 371 of instrument 13, and will not be described here.

Figure 28:
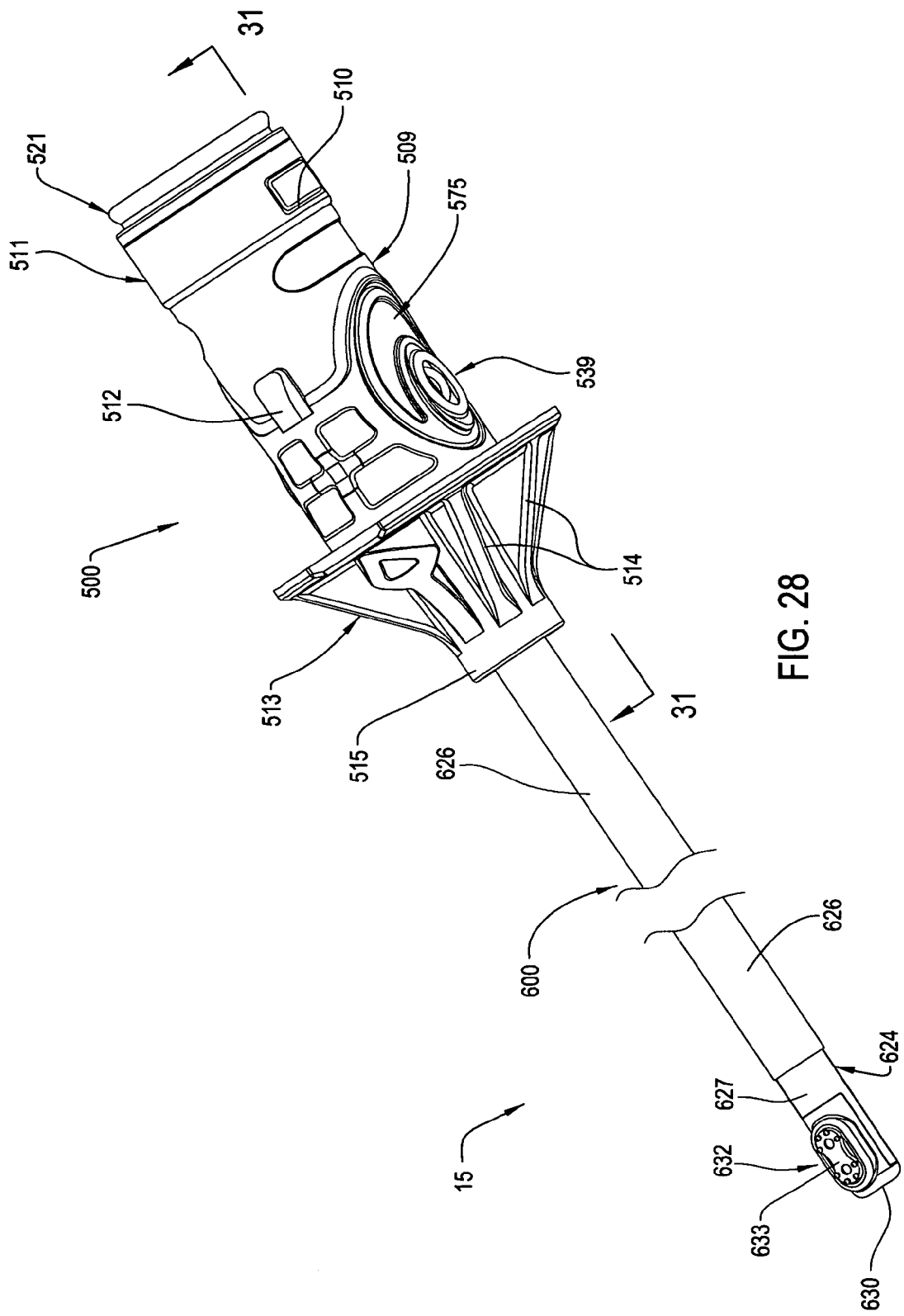
FIG. 28 is a perspective and fragmentary view of an electrosurgical instrument.
Figure 29:
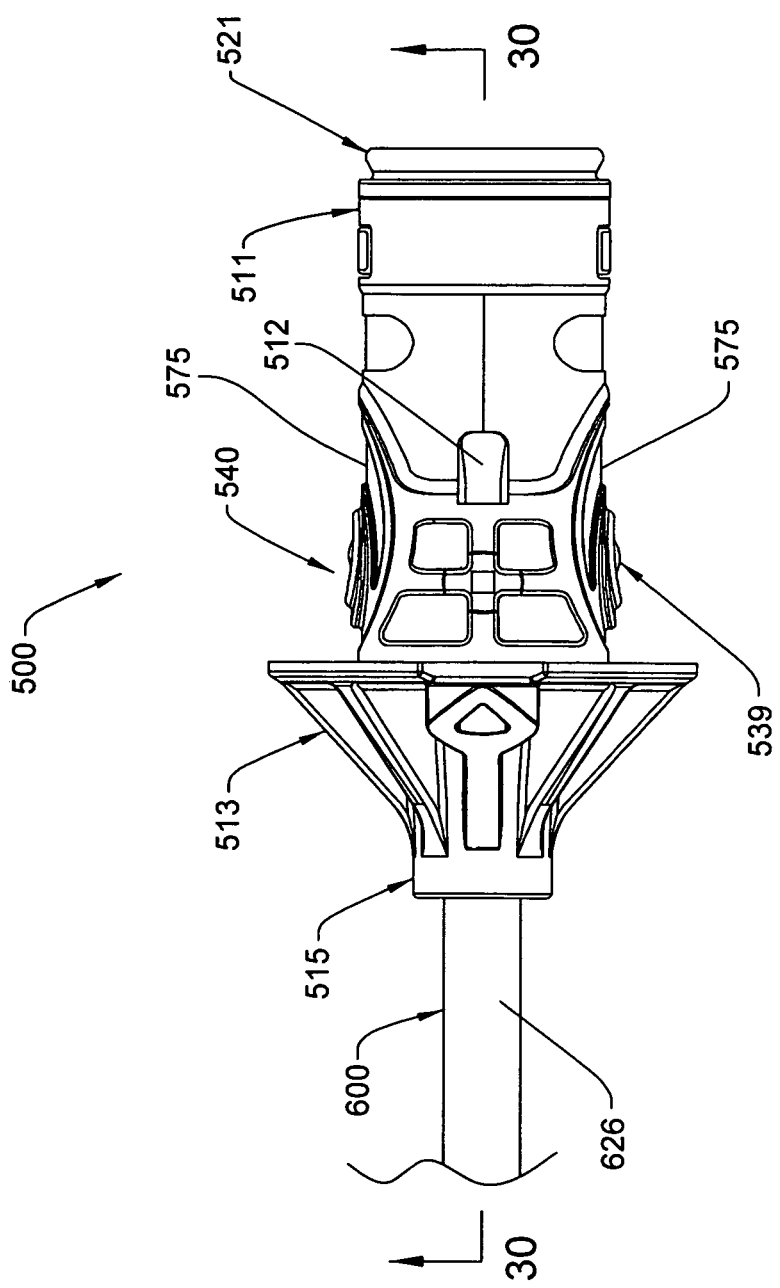
FIG. 29 is a fragmentary plan view of the electrosurgical instrument of FIG. 28.

Turning now to tube assembly 600 of instrument 15, and with reference to FIGS. 28 and 31, same includes an inner tube 620 defining a conduit 621 therein, an inner insulating tube 622 disposed over the inner tube 620, a hollow outer shaft 624 in which tubes 620 and 621 are disposed, and an outer insulating tube 626 which is disposed over outer shaft 624. In this regard, outer insulating tube 626 is disposed over the majority of the longitudinal extent of outer shaft 624, and a distal end 627 of outer shaft 624 is exposed to define a return electrode. An insulator cap 630 is seated within the open distal end 627 of outer shaft 624, and an electrode assembly 632 having an active electrode 633 is mounted within insulator cap 630 and has a tubular proximal end portion which is seated within the open distal end of inner tube 620.

In the illustrated embodiment, inner tube 620 and outer shaft 624 are constructed of conductive metal, such as stainless steel, and insulating tubes 621 and 626 are heat-shrink tubes. Inner tube 620 is disposed in electrical connection with electrode assembly 632 to provide a pathway for delivering electrical energy thereto. The above arrangement of tube assembly 600 is described in detail in U.S. Patent Publication No. 2006/0235377 which published on Oct. 19, 2006. The '377 publication is owned by the same assignee hereof, and is hereby incorporated by reference herein.

A proximal end 633A of insulating tube 622 and a proximal end 634 of inner tube 620 are fixedly mounted within bore 516 of base body 509, for example with adhesive. The insulating tube 622 terminates distally of the proximal end 634 of inner tube 620, and the exposed proximal end 634 of tube 620 is in electrical contact with arcuate inner leg 605 of spring contact 539. The outer insulating tube 626 terminates at end 626A distally of a proximal end 636 of outer shaft 624, and this exposed proximal end 636 is fixedly mounted within bore 516 adjacent support wall 544. An 0-ring 638 is provided around inner tubes 620 and 622, axially between the proximal end 636 of outer shaft 624 and support wall 544. The exposed proximal end 636 of outer shaft 624 is in electrical contact with arcuate inner leg 595 of contact 571.

The instrument 15 is secured to the handpiece 11 in a similar manner as instruments 13 and 14. Briefly, instrument 15 is attached to the handpiece 11 by inserting the hub assembly 500 into the open distal end 55 of collet 53 by aligning ears 512 of base body 509 with the respective channels 66. As instrument 15 is inserted into collet 53, the lower ear 512 engages the slider bar 203 of locking assembly 121, causing movement thereof in a counterclockwise direction. Once ear 512 is moved proximally past slider bar 203, the upper end 220 of slider bar 203 moves inwardly to prevent removal of tool 15 from handpiece 11. To release instrument 15 from handpiece 11, the user presses inwardly on the lock lever 200.

The securement of instrument 15 to handpiece 11 places contacts 570 and 571 in electrical contact with the respective contacts 80 of collet 53, which provides electrical power to active electrode 633 via the inner tube 620, and allows outer shaft 624 to function as a return via its return electrode 627.

The tool 15 may be used to cauterize or ablate tissue. These functions are controlled by the buttons 134 on handpiece 11 and control unit (CU). In this regard, if the surgeon selects the coagulation mode by pressing the appropriate button 134 on handpiece 11, then the control unit (CU) sends the appropriate signal to electrode 633 via the contact 80 located on collet 53, so as to apply electrical current to the targeted tissue through electrode 633. The surgeon can also select the ablation mode if tissue removal is desired by actuating the appropriate button 134 on handpiece 11, and can control the cut level by depressing a further button 134 on handpiece 11.

The proximal end 634 of inner tube 620 is positioned within counterbore 520 of hub base body 509, and when instrument 15 is attached to handpiece 11 as discussed above, suction conduit 621 of inner tube 620 is in communication with suction passage 31 of handpiece 11. Thus, when desirable or necessary, cut tissue and other surgical debris or fluids can be removed by suction through openings defined in the electrode 633 and conduit 621 of inner tube 620, through suction passage 31 and suction bore 30 of handpiece 11, and ultimately through the suction tube connected to fitting 32. Since instrument 15 does not include any component requiring the driving force of motor 20, this feature of handpiece 11 is not utilized with this instrument.

The handpiece 11, with its integrated electrical contact arrangements 79 provided in the collet 53, thus defines a universal handpiece which is usable with a variety of types of surgical instruments as described above, meaning that one handpiece is usable for a multitude of surgical procedures. The various surgical instruments or tools described herein are all adapted for use with the handpiece 11, and the appropriate instrument can thus be selected for the surgical procedure to be performed. These instruments may be disposable after one use. It is contemplated that other types of surgical instruments can be used with handpiece in addition to those described above, and the above are thus provided only as illustrative examples.

Although a particular preferred embodiment of the invention is disclosed in detail for illustrative purposes, it will be recognized that variations or modifications of the disclosed apparatus, including the rearrangement of parts, lie within the scope of the present invention.

What is claimed is:

1. A surgical tool arrangement comprising:
  a surgical instrument including a hub assembly defining a proximal end of said instrument and an elongate shaft assembly fixed to and projecting distally from said hub assembly, said shaft assembly at a distal end thereof defining an electrosurgical element for treating patient tissue; and
  a handpiece having an axis and including a housing having a proximal end and a distal end spaced therefrom, said distal end having an opening for receiving a portion of said hub assembly of said instrument, and an electrical contact arrangement mounted on said distal end and in communication with a control unit which selectively provides power to said contact arrangement, said contact arrangement including a contact member; said hub assembly of said instrument including an electrical contact arrangement disposed to mate with said contact arrangement of said handpiece to provide power to said electrosurgical element when said surgical instrument is mounted on said handpiece, said contact arrangement of said hub assembly having a contact member including a first outer leg disposed in electrical contact with said contact member of said handpiece and a second inner leg electrically connected to said electrosurgical element of said instrument, said second inner leg being connected to said first outer leg and supporting said first outer leg such that said first outer leg is disposed in substantially radially opposed relation with said second inner leg and such that when said portion of said hub assembly is engaged within said opening of said distal end of said handpiece, said contact member of said instrument is compressed and said first outer leg is biased substantially radially outwardly to maintain electrical contact with said contact member of said handpiece.

2. The arrangement of claim 1, wherein said distal end of said handpiece is tubular in configuration so as to define an inner circumference and an outer circumference, and said contact member of said handpiece is disposed adjacent said inner circumference, said hub assembly including a base body defining an outer circumference, and said first outer leg of said contact member of said hub assembly being disposed adjacent said outer circumference.

3. The arrangement of claim 1, wherein said hub assembly of said instrument includes a generally cylindrical base body defining a recess therein, said contact member of said hub assembly being mounted in said recess such that said first outer leg is biased radially outwardly in a direction away from the axis to maintain contact with said contact member of said handpiece.

4. The arrangement of claim 3, wherein said hub assembly includes a sealing member disposed in said recess in surrounding relation with said first outer leg of said contact member of said hub assembly.

5. The arrangement of claim 3, wherein said base body includes a support wall structure disposed in said recess, said support wall structure defining therein an outwardly opening slot in which said contact member of said hub assembly is disposed.

6. The arrangement of claim 5, wherein said base body is tubular in configuration and defines a generally hollow interior, said support wall structure defining an opening which permits communication between an inner end of said slot and said interior of said base body, said second inner leg of said contact member of said hub assembly having a portion which projects inwardly into said opening and is electrically connected to said electrosurgical element of said instrument.

7. The arrangement of claim 1, wherein said first inner leg and said second outer leg of said contact member of said hub assembly of said instrument are connected to one another by a bent portion of said contact member of said instrument so as to be disposed in opposed radial relation with one another, said first inner leg and said second outer leg extending substantially axially along said hub assembly.

8. The arrangement of claim 1, wherein said handpiece includes a locking mechanism disposed on said distal end for permitting removable attachment of said instrument to said handpiece.

9. The arrangement of claim 1, wherein said handpiece is defined by a generally tubular coupling member defining said opening therein and having a generally hollow interior, said contact member of said instrument being a first contact member and said electrosurgical element defining an active, energy-delivering electrode, said contact arrangement of said instrument including a second contact member having a first outer leg and a second inner leg electrically connected to a return electrode of said instrument, said coupling member defining a pair of bores oriented substantially radially with respect to the axis and mounting thereon said contact arrangement of said handpiece, said contact arrangement of said handpiece including a pair of button contacts respectively disposed in said bores for cooperation with the respective said first outer legs of said contact members of said instrument.

10. The arrangement of claim 9, wherein said bores of said coupling member communicate with said interior thereof, and said contact members of said handpiece are disposed in radially inner portions of said bores adjacent said interior.

11. The arrangement of claim 1, wherein said first outer leg is supported in a cantilevered manner from said second inner leg.

12. An electrosurgical instrument for use with a surgical handpiece, said instrument defining a longitudinal axis and comprising a hub assembly defining a proximal end of said instrument and a shaft assembly fixed to and projecting distally from said hub assembly, said shaft assembly at a distal end thereof defining an electrosurgical element for electrically treating patient tissue, said hub assembly comprising a generally cylindrical base body having a distal end mounting therein a proximal end of said shaft assembly and a proximal end spaced from said distal end and configured for mounting within a surgical handpiece, said hub assembly further comprising a spring-loaded electrical contact member, said contact member having an inner leg disposed in electrical contact with a conductive member of said shaft assembly electrically connected to said electrosurgical element and an outer leg, said inner leg being seated in a recess defined in said base body and connected to said outer leg to support said outer leg in substantially radially opposed relation with said inner leg, said outer leg projecting exteriorly of said base body for cooperation with a surgical handpiece, and a sealing member disposed in said recess in surrounding relation with a portion of said outer leg of said contact member.

13. The instrument of claim 12, wherein said inner and outer legs of said contact member are connected to one another by an intermediate portion of said contact member oriented transversely to the axis so as to be disposed radially in opposed relation with one another, said inner and outer legs extending substantially axially along said base body.

14. The instrument of claim 12, wherein said base body includes a support wall structure disposed in said recess, said support wall structure defining therein an outwardly opening slot in which said contact member is disposed.

15. The instrument of claim 14, wherein said base body is tubular in configuration and defines a generally hollow interior, said support wall structure defining an opening which permits communication between a lower end of said slot and said interior of said base body, said inner leg of said contact member having a portion which projects inwardly into said opening, said portion being disposed in electrical contact with said conductive member.

16. The instrument of claim 12, wherein said base body defines a pair of said recesses which open outwardly in a direction generally transverse to the axis, said electrosurgical element defining an active-energy delivering electrode, said contact member being a first contact member and said hub assembly comprising a second contact member having an inner leg disposed in electrical contact with a return electrode of said shaft assembly and an outer leg which projects exteriorly of said base body for cooperation with a surgical handpiece.

17. The instrument of claim 16, further including a pair of sealing members disposed in the respective said recesses and in surrounding relation with the respective said outer legs of said contact members.

18. The instrument of claim 12, wherein said outer leg is supported in a cantilevered manner from said inner leg.

19. A surgical tool arrangement comprising a handpiece defining a longitudinal axis, said handpiece including a housing having a proximal end and a distal end spaced therefrom and defined by a generally tubular side wall of said housing, said side wall defining an interior which opens axially and is configured to receive therein one of a plurality of surgical instruments usable with said handpiece, and a locking mechanism mounted on said distal end and including a lock lever mounted on said housing for pivoting movement relative thereto about a pivot axis, said lock lever having a first part disposed and configured for manipulation by a user and a second part, the pivot axis being disposed between said first and second parts, said lock lever having a locked position wherein a portion of said lock lever is disposed to engage said one surgical instrument to prevent removal thereof from said handpiece, said lock lever being movable into an unlocked position wherein said first part pivots in a first direction and said second part pivots in a second direction opposite the first direction to disengage said portion from said one surgical instrument to permit removal thereof from said handpiece.

20. The arrangement of claim 19, wherein said side wall defines an opening therein oriented generally transversely to the axis of said handpiece and communicating with said interior, said portion of said lock lever comprises a bar member having an outer end connected to said second part of said lock lever and an inner end movable within said opening and relative to said housing.

21. The arrangement of claim 20, wherein said outer end of said bar member is pivotably attached to said second part of said lock lever and is oriented transversely to said second part.

22. The arrangement of claim 20, further including a biasing member supported between said housing and said first part of said lock lever opposite said second part, said lock lever being pivotably movable about the pivot axis, the pivot axis being oriented transversely to the axis of the handpiece.

23. The arrangement of claim 22, wherein said lock lever mounts thereon a pivot pin which defines the pivot axis and said distal end of said housing defines therein an opening in which said pivot pin is disposed to permit pivoting movement of said lock lever about the pivot axis.

24. The arrangement of claim 19, wherein said one surgical instrument includes a hub assembly defining a proximal end of said instrument and including a base body defining an outer peripheral surface configured for cooperation with said interior of said handpiece, said base body mounting thereon a projection with which said portion of said lock lever engages in said locked position to prevent removal of said one surgical instrument from said handpiece.

25. The arrangement of claim 24, wherein said portion of said lock lever has an inner end disposed towards the axis and having a rounded surface, and said projection of said base body of said one surgical instrument has a ramped-shaped surface which diverges outwardly in a proximal to distal direction, said rounded surface engaging said ramped-shaped surface of said projection of said base body of said one surgical instrument during insertion of said one surgical instrument into said distal end of said handpiece housing.

26. The arrangement of claim 19, wherein said locking mechanism is biased in the locked position and is movable into the unlocked position by pressing said first part inwardly which causes said first part to pivot about the pivot axis in the first direction towards the axis of said handpiece and said second part to pivot about the pivot axis in the second direction away from the axis of said handpiece.

27. A surgical tool arrangement comprising a handpiece defining a longitudinal axis, said handpiece including a housing having a proximal end and a distal end spaced therefrom and defined by a generally tubular side wall of said housing, said side wall defining an interior which opens axially to define a surgical instrument-receiving opening, and a locking mechanism mounted on said distal end and including a lock lever mounted on said housing for pivoting movement relative thereto about a pivot axis, said lock lever having a first part disposed and configured for manipulation by a user and a second part, the pivot axis being disposed between said first and second parts, said lock lever having a locked position wherein a portion of said lock lever is disposed in a surgical instrument-engagement position, said lock lever being movable into an unlocked position wherein said first part pivots in a first direction and said second part pivots in a second direction opposite the first direction to move said lock lever into a surgical instrument-disengagement position.

* * * * *